United States Patent [19]

Boothroyd et al.

[11] Patent Number: 4,743,554

[45] Date of Patent: May 10, 1988

[54] RECOMBINANT DNA EXPRESSION VECTOR ENCODING FOR FOOT AND MOUTH DISEASE VIRUS PROTEINS

[76] Inventors: John C. Boothroyd, 7 Westgate Road, Beckenham, Kent; George A. M. Cross, 37a The Grove, Biggin Hill, Westerham, Kent; Michael D. Highfield, 107 South Eden Park Road; Michael D. Winther, Flat 3a, South Eden Park Road, both of Beckenham, Kent; David J. Rowlands, Tile House, 98 Busbridge Lane, Godalming, Surrey; Fred Brown, "Syndal" Glaziers Lane, Normandy, Surrey, England; Timothy J. R. Harris, 70 Minley Road, Cove, Farnborough, Hants, all of England

[21] Appl. No.: 728,464

[22] Filed: May 1, 1985

Related U.S. Application Data

[63] Continuation of Ser. No. 299,884, Sep. 8, 1981.

[51] Int. Cl.[4] .................. C12N 1/00; C12N 15/00; C12N 1/20; A61K 39/00
[52] U.S. Cl. .................. 435/253; 435/172.3; 435/320; 935/11; 935/12; 424/88; 514/12
[58] Field of Search .............. 435/172.3, 68, 70, 253, 435/317; 536/27; 935/10, 11, 12, 9

[56] References Cited

PUBLICATIONS

Burrell et al, Nature, vol. 279, pp. 43–47, May 1979.
Porter et al, Nature, vol. 282, pp. 471–477, Nov. 1979.
Porter et al, Nature, vol. 276, Nov. 1978.
Bachrach et al, Intervirology 12: 65–72 (1979).
Bachrach et al, Perspectives in Virology, vol. 10, pp. 147–159 edited by Morris Pollard. Raven Press 1978.
Kacian et al, Proc. Nat. Acad. Sci. USA, vol. 73, No. 7, pp. 2191–2195, Jul. 1976.
Sanger et al, Journal of Virology, vol. 33, No. 1, pp. 59–68, Jan. 1980.
Higuchi et al, PNAS, vol. 73, No. 9, pp. 3146–3150, Sep. 1976.
Strohmaier et al, Biochem. and Biophys. Rese. Comm., vol. 85, pp. 1640–1645 (1978).
Doll et al, J. Gen. Virol., vol. 41, pp. 395–404 (1978).
Higuchi et al, Pro. Natl. Acad. Sci: USA, vol. 73, pp. 3146–3150, Sep. 1976.

*Primary Examiner*—Alvin E. Tanenholtz
*Attorney, Agent, or Firm*—Donald Brown

[57] ABSTRACT

A DNA molecule comprising a nucleotide sequence substantially corresponding to all or a portion of foot and mouth disease virus RNA and in particular coding for at least one protein of foot and mouth disease virus. The DNA molecule can be inserted into a DNA cloning vehicle capable of expressing the DNA molecule, after a suitable host cell has been transformed by the cloning vehicle. The expression product can be incorporated into a vaccine for stimulating antibodies against FMDV. Methods for producing the DNA molecule, recombinant cloning vehicle and transformed host cell are described.

3 Claims, 26 Drawing Sheets

```
                                              350
                T TCC ACG GAC ACA ACT TCA ACA CAC ACA ACC AAC ACC
                  Ser Thr Asp Thr Thr Ser Thr His Thr Thr Asn Thr
                                         400
CAA AAC AAC GAC TGG TTT TCA AAA CTT GCC AGT TCG GCT TTT ACC GGT
Gln Asn Asn Asp Trp Phe Ser Lys Leu Ala Ser Ser Ala Phe Thr Gly
                                         450
CTG TTC GGT GCA CTT CTC GCC|GAC AAG AAG ACG GAA GAG ACT ACG CTT
Leu Phe Gly Ala Leu Leu Ala|Asp Lys Lys Thr Glu Glu Thr Thr Leu
                    ←VP4 | VP2→  500
CTG GAA GAC CGC ATC CTC ACT ACC CGC AAC GGG CAC ACC ACT TCG ACC
Leu Glu Asp Arg Ile Leu Thr Thr Arg Asn Gly His Thr Thr Ser Thr

ACC CAG TCG AGT GTG GGA GTC
Thr Gln Ser Ser Val Gly Val
```

*FIG. 4*

```
ATCATATGCA TATATGAGGA ACGGCTGGGA TGTTGAGGTA TCTGCCGTCG GCAACCAGTT CAACGGCGGG
 SerTyrAla TyrMetArgA snGlyTrpAs pValGluVal SerAlaValG lyAsnGlnPh eAsnGlyGly

TGCCTTCTGG TGGCCATGGT GCCAGATGGG AAGGCATTTG ACACACGTGA AAAATACCAG CTTACCCTTT
CysLeuLeuV alAlaMetVa lProGluTrp LysAlaPheA spThrArgGl uLysTyrGln LeuThrLeuP

TCCCACACCA GTTTATTAGC CCCAGAACTA ACATGACTGC CCACATCACG GTACCGTATC TTGGTGTGAA
heProHisGl nPheIleSer ProArgThrA snMetThrAl aHisIleThr ValProTyrL euGlyValAs

CAGGTACGAT CAGTACAAGA AACACAAACC TTGGACACTG GTTGTCATGG TACTATCACC CCTCACGGTC
nArgTyrAsp GlnTyrLysL ysHisLysPr oTrpThrLeu ValValMetV alLeuSerPr oLeuThrVal

AGCAACACTG CCGCCCCACA AATCAAGGTC TACGC
SerAsnThrA laAlaProGl nIleLysVal TyrAla
```

*FIG. 5*

GGGCGCTTTA CAAACCTATT GGACGTGGCC GAAGCATGTC CCACCTTTCT TCGTTTCGAC GATGGGAAAC
GlyArgPheT hrAsnLeuPh eAspValAla GluAlaCysP roThrPheLe uArgPheAsp AspGlyLysP
 GlyAlaLeu GlnThrTyrT rpThrTrpPr oLysHisVal ProProPheP heValSerTh rMetGlyAsn

CGTACGTCGT TACGCGGGCA GACGACACCC GTCTTTTGGC CAAGTTTGAT GTCTCCCTTG CCGCAAAACA
roTyrValVa lThrArgAla AspAspThrA rgLeuLeuAl aLysPheAsp ValSerLeuA LaAlaLysHi
ArgThrSerL euArgGlyGl nThrThrPro ValPheTrpP roSerLeuMe tSerProLeu ProGlnAsnT

CATGTTCAAC ACATACCTAT CAGGGATTGC ACAGTACTAC ACACAGTACT CTGGTACTAT CAACCTGCAC
sMetPheAsn ThrTyrLeuS erGlyIleAl aGlnTyrTyr ThrGlnTyrS erGlyThrIl eAsnLeuHis
hrCysSerTh rHisThrTyr GlnGlyLeuH isSerThrTh rHisSerThr LeuValLeuS erThrCysTh

TTCGTGTTCA CAGGCTCCAC TGACT
PheValPheT hrGlySerTh rAsp
rSerCysSer GlnAlaProL euThr

FIG. 6

GACTCGCTCT CCAGTCTCTT TCACGTGCCG GCCCCCGCCT TCAGTTTCGG AGCTCCGGTT CTGTTGGCCG
AspSerLeuS erSerLeuPh eHisValPhe AlaProAlaP heSerLeuGl yAlaProVal LeuLeuAlaG
 ThrArgSer ProValSerP heThrCysAr gProProPro SerValSerG luLeuArgPh eCysTrpPro

GGTTGGTCAA GGTCGCCTCG AGTTTCTTCC GGTCCACACC CGAAGACCTT GAGAGAGCAG AGAAACAGCT
lyLeuValLy sValAlaSer SerPhePheA rgSerThrPr oGluAspLeu GluArgAlaG luLysGlnLe
GlyTrpSerA rgSerProAr gValSerSer GlyProHisP roLysThrLe uArgGluGln ArgAsnSerS

CAAAGCACGT GACATTAACG ACATCTTGCC ATTCTCAAGA ACGGCGAGTG GCTGGTCAAA CTG
eLysAlaArg AspIleAsnA spIleLeuPr oPheSerArg ThrAlaSerG lyTrpSerAs n
erLysHisVa lThrLeuThr ThrSerCysH isSerGlnGl uAlaAlaVal AlaGlyGlnT hr

FIG. 7

```
                          5                     10                    15
A₆₁  Thr Thr Thr Thr Gly Glu Ser Ala Asp Pro Val Thr Thr Thr Val Glu Asn Tyr

A₁₂  Thr Thr Cys Thr Gly Glu Cys Ala Asp Pro Val Val Thr Cys Val Glu Asn Tyr

O₁K  Thr Thr Ser Ala Gly Glu Lys Ala Asp Pro Val Thr Thr Thr Val Glu Asn Tyr

Ser
O₁B  Thr Thr Ser Ala Gly Glu Ser Ala Asp Pro Val Val Asp Ser Val Glu Ser Tyr

Asp                                    Asn
C₃R  Thr Thr Thr Cys Gly Glu Cys Ala Ser Pro Val Val Thr Thr Val Glu Ser Tyr 20                  25                  30                  35
A₆₁  Gly Gly Asp Thr Gln Val Gln Arg Arg His His Thr Asp Val Gly Phe Ile Met

A₁₂  Gly Gly Glu Glu Glu Val Gln Pro

O₁K  Gly Gly Glu Thr Gln Ile Gln Arg Arg Gln His Thr Asp Val Trp Phe Ile Met

Val Gln
O₁B  Gly Gly Glu Glu Glu Leu Thr Pro

Gln
C₃R  Gly Gly Glu Glu Glu Val Asp
```

Amino acids underlined in the A₆₁ sequence are those which are common to all five stains. Amino acids underlined in the other strain sequences are those which are homologous between that strain and A₆₁.

HOMOLOGY

| | | | |
|---|---|---|---|
| $A_{61}:A_{12}$  18/26 (69%) | $A_{12}:O_{1K}$  17/26 (65%) | $O_{1K}:O_{1B}$  16/26 (62%) | |
| $A_{61}:O_{1K}$  29/36 (81%) | $A_{12}:O_{1B}$  19/26 (73%) | $O_{1K}:C_{3R}$  16/25 (64%) | |
| $A_{61}:O_{1B}$  15/26 (58%) | $A_{12}:C_{3R}$  20/25 (80%) | $O_{1B}:C_{3R}$  18/25 (72%) | |
| $A_{61}:C_{3R}$  18/25 (72%) | | | |

FIG. 8

```
TCC AAT TGC CCC CGG ACA CAA ACC ACT ACT ACT GGG GAG TCC GCA GAC
Ser Asn Cys Pro Arg Thr Gln Thr Thr Thr Thr Gly Glu Ser Ala Asp
                            VP3 VP1

CCT GTC ACC ACC ACC GTG GAG AAC TAC GGC GGT GAT ACA CAA GTC CAG AGA
Pro Val Thr Thr Thr Val Glu Asn Tyr Gly Gly Asp Thr Gln Val Gln Arg

CGT CAC CAC ACG GAC GTC GGC TTC ATT ATG GAC CGA TTT GTG AAG ATA AAC
Arg His His Thr Asp Val Gly Phe Ile Met Asp Arg Phe Val Lys Ile Asn

AGC CTG AGC CCC ACA CAT GTC ATT GAC CTC ATG CAA ACC CAC AAA CAC GGG
Ser Leu Ser Pro Thr His Val Ile Asp Leu Met Gln Thr His Lys His Gly

ATC GTG GGT GCG TTA CTG CGT GCA GCC ACG TAC TAC TTC TCC GAC TTG GAG
Ile Val Gly Ala Leu Leu Arg Ala Ala Thr Tyr Tyr Phe Ser Asp Leu Glu

ATT GTT GTG CGG CAC GAT GGT
Ile Val Val Arg His Asp Gly
```

| ACC | ATT | GCC | CCA | ACC | TAC | GTT | CAC | GTG | GCT |
|-----|-----|-----|-----|-----|-----|-----|-----|-----|-----|
| Asn | Ile | Ala | Pro | Thr | Tyr | Val | His | Val | Ala |
| GGA | GAG | CTT | CCC | TCG | AAA | GAG | GGG | ATT | TTC |
| Gly | Glu | Leu | Pro | Ser | Lys | Glu VP2 | Gly VP3 | Ile | Phe |
| CCA | GTT | GCA | TGC | GCA | GAC | GGT | TAC | GGA | GGA |
| Pro | Val | Ala | Cys | Ala | Asp | Gly | Tyr | Gly | Gly |
| CTG | GTG | ACA | ACA | GAC | CCG | AAA | ACA | GCT | GAC |
| Leu | Val | Thr | Thr | Asp | Pro | Lys | Thr | Ala | Asp |
| CCT | GTT | TAC | GGT | AAG | GTG | TAT | AAC | CCG | CCC |
| Pro | Val | Tyr | Gly | Lys | Val | Tyr | Asn | Pro | Pro |
| AAG | ACC | AAC | TAC | CCC | | | | | |
| Lys | Thr | Asn | Tyr | Pro | | | | | |

FIG. 12a

KEY *** = STOP CODON
___ = NUCLEOTIDE NOT KNOWN

```
SER VAL *** LEU ASP ASN GLY GLN THR PHE TRP ILE LEU ASP LYS THR GLY ALA SER HIS
LEU PHE ASP TRP THR ASP LYS ASN LEU PRO PHE GLY TYR LEU THR LYS LEU GLU LEU PRO THR
    CYS LEU THR GLY GLN ARG THR                     *** GLN ASN TRP SER PHE PRO PRO
TCTGTTTGACTGGACTGACAACGGACAAACCTTTTGGATACTTGACAAAACTGGAGCTTCCCAC
                    310                 320                 330                 340                 350                 360

ARG SER PRO ARG CYS LEU ARG ALA PRO VAL ASP SER         ASN HIS MET HIS ILE *** GLY
ASP HIS HIS GLY VAL PHE SER SER GLY HIS THR CYS GLY LEU     ILE ILE CYS ILE TYR GLU GLU
    ILE THR THR VAL SER SER GLY THR CYS GLY HIS THR CYS GLY LEU GLU SER TYR ALA TYR MET ARG ASN
CGATCACCACGGTCTTCGGCACCTGGACTC - - - GAATCATATGCATATGAGGA
                    370                 380                 390                 400                 410                 420

THR ALA GLY MET LEU ARG TYR VAL PRO SER ALA THR SER SER THR ALA GLY ALA PHE TRP
ARG LEU GLY CYS *** GLY MET CYS ARG ARG GLN PRO VAL GLN ARG ARG GLY VAL PRO SER GLY
GLY TRP ASP VAL CYS VAL GLU CYS ALA VAL GLY ASN GLN PHE ASN GLY GLY CYS LEU LEU VAL
ACGGCTGGGATGTTGAGGTATGTGCCGTCGGCAACCAGTTCAACGGGGTGCCTTCTGG
                    430                 440                 450                 460                 470                 480

FIG. 12a CONTINUED
```

```
TRP PRO TRP CYS GLN SER GLY ARG HIS LEU THR HIS VAL LYS ASN THR SER LEU PRO PHE
    GLY HIS GLY ALA ARG VAL GLU GLY GLY ILE *** HIS THR ARG *** LYS ILE PRO ALA TYR PRO PHE
        ALA MET VAL PRO GLU TRP LYS ALA PHE ASP THR ARG GLU LYS TYR GLN LEU THR LEU PHE
TGGCCATGGTGCCAGAGTGGAAGGCATTTGACACACGTGAAAAATACCAGCTTACCCTTT
             490                  500                  510                 520                 530                 540

SER HIS THR SER LEU LEU ALA PRO GLU LEU THR *** LEU PRO THR SER ARG TYR ARG ILE
    PRO THR PRO VAL TYR *** PRO GLN ASN *** HIS ASP CYS PRO HIS HIS GLY THR VAL SER
        PRO HIS GLN PHE ILE SER PRO ARG THR ASN MET THR ALA HIS ILE THR VAL PRO TYR LEU
TCCCACACCAGTTTATTAGCCCCAGAAACTAACATGACTGCCCACATCACGGTACCGTATC
             550                 560                  570                 580                 590                 600

LEU VAL *** THR GLY THR ILE SER THR ARG ASN THR ASN LEU GLY HIS TRP LEU SER TRP
    TRP CYS GLU GLN VAL ARG SER VAL GLN THR GLN THR LEU ASP THR GLY CYC HIS GLY
        GLY VAL ASN ARG TYR ASP TYR GLN LYS LYS HIS PRO TRP THR LEU VAL VAL MET VAL
TTGGTGTGAACAGGTACGATCAGTACAAGAAACACAAACCTTGGACACTGGTTGTCATGG
             610                 620                  630                 640                  650                 660

TYR TYR HIS PRO SER ARG SER ALA THR LEU PRO PRO HIS LYS SER ARG SER THR PRO THR
    THR ILE THR PRO HIS GLY GLN HIS CYS ARG PRO THR ASN GLN GLY LEU ARG GLN HIS
        LEU SER PRO LEU THR VAL SER ASN THR ALA ALA PRO GLN ILE LYS VAL TYR ALA ASN ILE
TACTATCACCCCTCACGGTCAGCAACACTGCCGCCCACAAATCAAGGTCTACGCCAACA
             670                 680                  690                 700                 710                  720

LEU PRO GLN PRO THR PHE THR TRP LEU GLU SER PHE PRO ARG LYS ARG GLY PHE SER GLN
    CYS PRO ASN LEU ARG SER ARG ARG GLY ALA SER LEU PRO SER GLU GLY ASP PHE PRO SER
        ALA PRO THR TYR VAL HIS VAL GLY LEU GLU LEU PRO SER LYS GLU ARG GLY ILE PHE PRO VAL
TTGCCCCAACCTACGTTCACGTGGCTGGAGAGCTTCCCTCGAAAGAGGGGATTTTCCCAG
             730                 740                  750                 760                 770                 780
                                                                                                        VP2│VP3
```

FIG. 12b

```
LEU  HIS  ALA  GLN  THR  VAL  THR  GLU  ASP  TRP  ***  GLN  GLN  THR  ARG  LYS  GLN  LEU  THR  LEU
CYS  MET  ARG  ARG  ARG  LEU  ARG  ARG  THR  GLY  ASP  ASN  ARG  PRO  GLU  ASN  SER  ***  PRO  CYS
ALA  CYS  ALA  ASP  GLY  TYR  GLY  GLY  VAL  LEU  THR  THR  ASP  PRO  LYS  THR  ALA  ASP  PRO  VAL
TTGCATGCGCAGACGGTTACGGAGGACTGGTGACAACAGACCCGAAAACAGCTGACCCTG
            790                  800                  810                  820                  830                  840

PHE  THR  VAL  ARG  CYS  ILE  THR  ARG  PRO  ARG  PRO  THR  THR  PRO  GLY  ALA  LEU  GLN  THR  TYR
LEU  ARG  ***  GLY  VAL  ***  PRO  ALA  GLN  ASP  PRO  ARG  ALA  LEU  TYR  LYS  PRO  ILE
TYR  GLY  LYS  VAL  TYR  ASN  PRO  LYS  THR  ASN  TYR  PRO  GLY  ARG  PHE  THR  ASN  LEU  LEU
TTTACGGTAAGGTGTATAACCCGCCCAAGACCAACTACCCCGGGCGCTTTACAAACCTAT
            850                  860                  870                  880                  890                  900

TRP  THR  TRP  PRO  LYS  HIS  VAL  PRO  PRO  PHE  PHE  VAL  SER  THR  MET  GLY  ASN  ARG  THR  SER
GLY  ARG  GLY  ARG  SER  MET  SER  HIS  LEU  SER  PHE  ARG  ARG  TRP  GLU  THR  VAL  ARG  ARG
ASP  VAL  ALA  GLU  ALA  CYS  PRO  THR  PHE  LEU  ARG  PHE  ASP  ASP  GLY  LYS  PRO  TYR  VAL  VAL
TGGACGTGGCCGAAGCATGTCCCACCTTTCTTCGTTTCGACGATGGGAAACCGTACGTCG
            910                  920                  930                  940                  950                  960

LEU  ARG  GLY  GLN  THR  HIS  THR  PRO  VAL  PHE  TRP  PRO  SER  LEU  MET  SER  PRO  LEU  PRO  GLN  ASN
TYR  ALA  GLY  ARG  ARG  HIS  PRO  SER  PHE  GLY  GLN  VAL  ***  CYS  LEU  PRO  CYS  ARG  LYS  THR
THR  ARG  ALA  ASP  ASP  THR  ARG  LEU  LEU  ALA  LYS  SER  ASP  VAL  SER  LEU  ALA  ALA  LYS  HIS
TTACGCGGGCAGACGACACCCGTCTTTTGGCCAAGTTTGATGTCTCCCTTGCCGCAAAAC
            970                  980                  990                  1000                 1010                 1020

THR  CYS  PRO  THR  HIS  THR  TYR  GLN  GLY  LEU  HIS  SER  THR  HIS  SER  THR  LEU  VAL  LEU
HIS  VAL  GLN  HIS  ILE  PRO  ILE  ARG  ASP  CYS  THR  VAL  LEU  HIS  THR  VAL  LEU  TRP  TYR  TYR
MET  SER  ASN  THR  TYR  LEU  SER  GLY  ILE  ALA  GLN  TYR  THR  THR  GLN  TYR  SER  GLY  THR  ILE
```

```
ALA SER GLN LEU THR PRO GLY HIS LYS PRO LEU LEU LEU GLY SER PRO GLN THR LEU SER
    PRO PRO ASN *** PRO PRO ASP THR ASN HIS TYR TYR THR TRP GLY VAL SER PRO ARG ARG ASP PRO VAL HIS
    LEU PRO ILE ASP PRO ARG THR GLN THR THR THR GLY GLU SER ALA ALA ASP PRO VAL THR
GCCTCCCAATTGACCCCCGGACACAAACCACTACTGGGAGTCCGCAGACCCTGTCA
          1390                1400              1410              1420              1430            1440
                                          VP3|VP1
PRO PRO PRO ARG THR TRP ARG THR THR ALA VAL ILE HIS LYS SER ARG ASP VAL THR THR ARG THR
    HIS HIS ARG GLY LEU ARG ARG *** TYR THR SER PRO GLU THR SER PRO HIS GLY ARG
    THR THR VAL GLU ASN TYR GLY ASP THR GLN VAL GLN ARG ARG HIS HIS THR ASP VAL
CCACCACCGTGGAGAACTACGGCGGTGATACACAAGTCCAGAGACGTCACCACGGACG
          1450              1460              1470              1480              1490              1500

SER ALA SER LEU TRP THR ASP LEU *** ARG *** THR ALA *** ALA PRO HIS MET SER LEU
    ARG LEU HIS TYR GLY PRO ILE CYS GLU ASP LYS GLN PRO GLU PRO HIS THR CYS HIS ***
    GLY PHE ILE MET ASP ARG PHE VAL LYS ASN SER LEU SER PRO HIS VAL ILE ASP
TCGGCTTCATTATGGACCGATTTGTGAAGATAAACAGCCTGAGCCCCACACATGTCATTG
          1510              1520              1530              1540              1550              1560

THR SER CYS LYS PRO THR ASN THR GLY ASP SER TRP VAL ARG TYR CYS VAL GLN PRO ARG THR
    PRO HIS ALA ASN PRO GLN THR ARG ARG GLY CYS VAL THR ALA CYS SER HIS VAL LEU
    LEU MET GLN THR HIS HIS LYS HIS GLY ILE VAL GLY ALA LEU ARG ALA ALA THR TYR TYR
ACCTCATGCAAACCCACAAACACGGGATCGTGGGTGCGTTACTGCGTGCCAGCCACGTACT
          1570              1580              1590              1600              1610              1620
```

FIG. 12c CONTINUED

```
THR SER PRO THR TRP ARG LEU LEU CYS GLY THR MET VAL  ***           LEU GLY ALA
 LEU LEU ARG LEU GLY ASP CYS ALA ALA ARG TRP  ***           ASP TRP VAL PRO
  PHE SER ASP LEU GLU ILE VAL VAL ARG HIS ASP GLY            LEU THR GLY CYS PRO
A C T T C T C C G A C T T G G A G A T T G T T G T G C G G C A C G A T G G T A A - C T G A C T G G G T G C C C - - -
            1630              1640              1650              1660              1670              1680

1690              1700              1710              1720              1730              1740

ARG HIS THR ALA CYS TRP GLN LEU CYS THR THR GLY
                                                     ALA THR PRO ARG VAL GLY ASN CYS VAL ARG ARG ASP
                                                      PRO HIS ARG VAL -LEU ALA THR VAL TYR ASP GLY THR
- - - C G C C A C A C C G G C G T T G G C A A C T G T A C G A C G G G A
       1750              1760              1770              1780              1790              1800
                                                                                          CORRECT READING
                                                                                          FRAME UNKNOWN
GLN THR SER THR PRO GLN ARG
 LYS GLN VAL LEU ARG SER ASP
  ASN LYS TYR SER ALA ALA
C A A A C A A G T A C T C C G C A G C G A T - - -
            1810              1820              1830              1840              1850              1860

1870              1880              1890              1900              1910              1920

1930              1940              1950              1960              1970              1980

1990              2000              2010              2020           | 2030              2040
                                                                           | POSSIBLE C-TERMINAL
                                                                           | END OF VP1

FIG. 12d
```

```
                  ILE GLY THR ALA SER ARG PRO SER GLU VAL CYS MET VAL ASP
                  T A T C G G T A C C G C C T C G C G A C C C A G C G A G G T G T G T A T G G T A G A
                          20                  30                  40                  50                  60

GLY THR ASP MET CYS LEU ALA ASP PHE HIS ALA GLY ILE PHE MET LYS GLY GLN GLU HIS
C G G C A C G G A C A T G T C T T G C T G A T T T C C A C G C A G G C A T T T C A T G A A A G G A C A G G A A C A
          70                  80                  90                  100                 110                 120

ALA VAL PHE ALA CYS VAL THR SER ASP SER VAL PRO TYR ALA ILE ASP ASP GLU ASP PHE TYR
C G C A G T G T T C G C G T G T G T C A C C T C A G A C A G C G T G C C G T A C G C G A T T G A C G A C G A G G A C T T T T A
          130                 140                 150                 160                 170                 180

PRO TRP THR PRO ASP TRP LYS THR GLN VAL LEU VAL PHE VAL PRO TYR ASP GLN· GLU PRO LEU
C C C G T G G A C G C C T G A C C C A T C G G A C A C A G G T C T T G G T A T T T G T C C C G T A C G A T C A A G A A C C A C T
    p20       190                 200                 210                 220                 230                 240

ASN GLY ASP TRP LYS THR GLN VAL ASN GLN VAL LYS LEU LYS LYS GLY ALA GLY GLN SER SER PRO
C A A T G G G A C T G G A A A A C A C A G G T T C A G A A G A A G C T C A A G G G T G C T G G G C A G T C C A G C C C
          250                 260                 270                 280                 290                 300
                          POSITION OF N-TERMINAL OF VP1

ALA THR GLY SER GLN ASN GLY ASN THR GLY SER ILE ILE ILE ASN ASN TYR TYR MET
A G C A A C C G G C T C G C A G A A C G G C A A C A C T G G C A G C A T A A T T A A C A A C T A C T A C A T
          310                 320                 330                 340                 350                 360

GLN GLN TYR GLN ASN SER · MET SER THR GLN LEU GLY ASP ASN THR ILE SER GLY GLY SER
G C A G C A A T A C C A G A A C T C T A T G A G C A C A C A G C T T G G T G A C A A T A C C A T C A G T G G A G G C T C
          370                 380                 390                 400                 410                 420
```

FIG. 13a

```
ASN GLU GLY SER THR ASP THR THR SER THR HIS THR THR ASN THR GLN ASN ASN ASP TRP
C A A C G A G G G C T C C A C G G A C A C A A C T T C A A C A C A C A A C A A C C A A A C A A A A C A A C G A C T G
                    430             440             450             460             470             480
PHE SER LYS LEU ALA SER SER ALA PHE THR GLY LEU PHE GLY ALA LEU LEU      VP4|VP2
                                                                              ALA ASP LYS
G T T T T C A A A A C T T G C C A G T T C G G C T T T T A C C G G T C T G T T C G G T G C A C T T C T C G C C G A C A A
                    490             500             510             520             530             540

LYS THR GLU GLU THR LEU LEU GLU ASP ARG ILE LEU THR THR ARG ASN GLY HIS THR
G A A G A C G G A A G A G A C T A C G C T T C T G G A A G A C C G C A T C C T C A C T A C C C G C A A C G G G C A C A C
                    550             560             570             580             590             600
```

FIG. 13a CONTINUED

```
LEU VAL SER ALA PHE GLU LEU ALA THR GLY VAL LYS ALA ILE ARG THR GLY LEU ASP
GTTGGTGTCCGCTTTTGAGGAATTGGCCACTGGGGTTAAAGCTATCAGAACCGGTCTCGA
        2650              2660              2670              2680              2690              2700

GLU ALA LYS PRO TRP TYR LYS ILE LYS LEU LEU SER ARG LEU SER CYS MET ALA ALA
TGAGGCCAAAACCCTGGTACAAGCTCATCAAGCTCCTAAGCCGTCTGTCTCGTGCATGGCCGC
        2710              2720              2730              2740              2750              2760

VAL ALA ALA ARG SER LYS ASP PRO VAL LEU VAL ALA ILE MET LEU ALA ASP THR GLY LEU
TGTGGCAGCACGGGTCCAAGGACCCAGTCCCTTGTGGCCATCATGCTGGCCGACACCGGTCT
        2770              2780              2790              2800              2810              2820
```

FIG. 13d CONTINUED

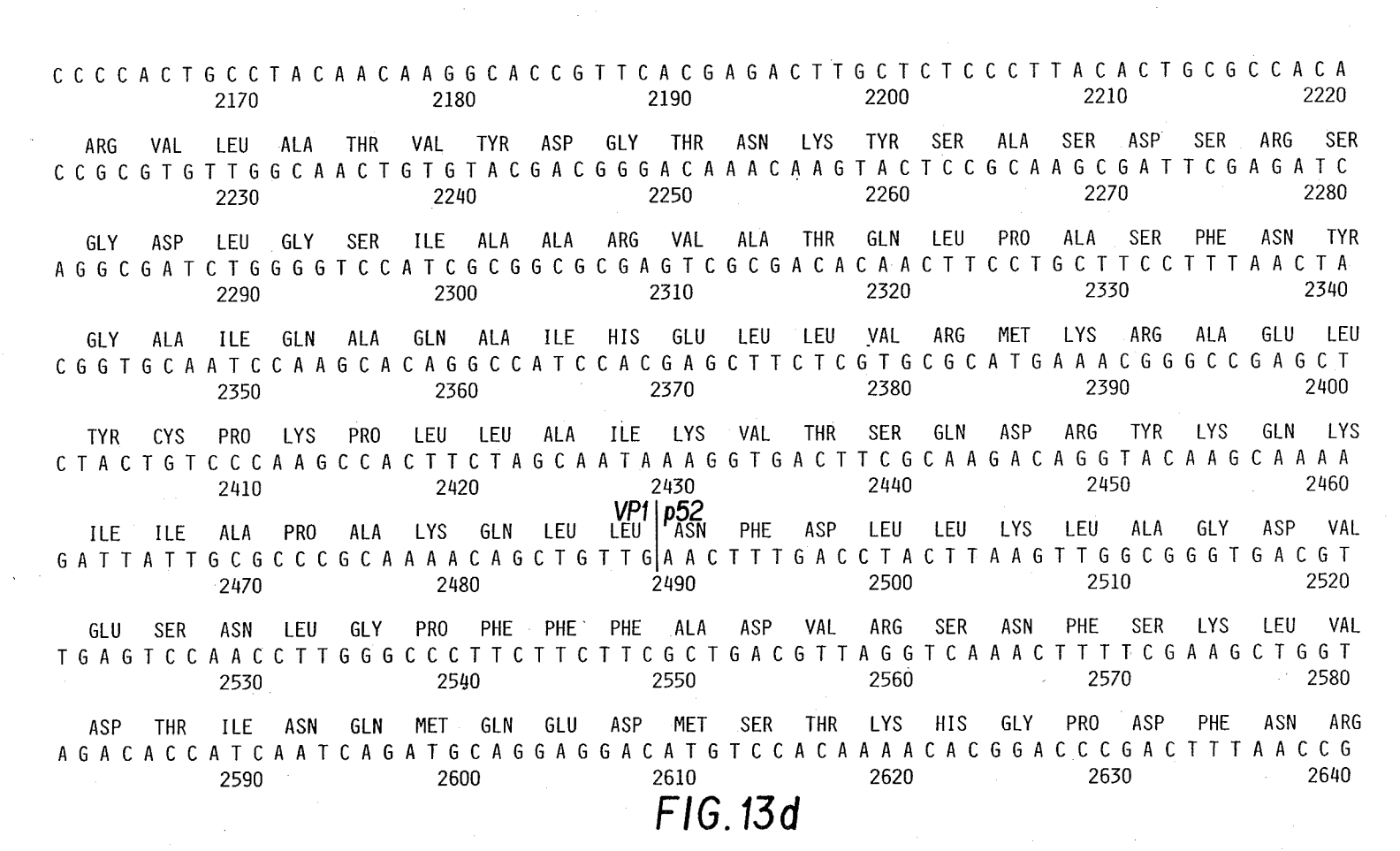

```
                                                                    SER
                                                                ARG 2280
                                                            SER 2220
                                                        ASP
                                                    SER
                                                ALA
                                            TYR
                                        LYS
                                    ASN
                                GLY
                            ASP
                        TYR
                    VAL
                THR
            ALA
        LEU
    VAL
ARG
```

(Unable to fully OCR this dense nucleotide/amino acid sequence figure.)

FIG. 13d

```
THR GLY GLU SER ALA ASP PRO VAL THR THR THR VAL GLU ASN TYR GLY GLY ASP THR GLN
T AC T GGG GAG TCC GCA GAC CCT GTC ACC ACC ACC GTG GAG AAC TAC GGC GGT GAT ACA CA
        1870            1880            1890            1900            1910            1920

VAL GLN ARG ARG HIS HIS THR ASP VAL GLY PHE ILE MET ASP ARG PHE VAL LYS ILE ASN
A GTC CAG AGA CGT CAC CAC ACG GAC GTC GGC TTC ATT ATG GAC CGA TTT GTG AAG ATA AA
        1930            1940            1950            1960            1970            1980

SER LEU SER PRO THR HIS VAL ILE ASP MET LEU ASP THR HIS LYS HIS GLY ILE VAL GLY
C AGC CTG AGC CCC ACA CAC ATG TCA TTG ACC TCA TTG CAA ACC CAC AAA CAC GGG ATC GTG GG
        1990            2000            2010            2020            2030            2040

ALA LEU LEU ARG ALA ALA THR TYR TYR PHE SER ASP LEU GLU ILE VAL VAL ARG HIS ASP
T GCG TTA CTG CGT GCA GCC ACG TAC TAC TTC TCT CCG ACT TGG AGA TTG TTG CGG CAC GA
        2050            2060            2070            2080            2090            2100

GLY ASN LEU THR TRP VAL PRO ASN GLY ALA ALA PRO GLU ALA ALA LEU SER ASN THR SER ASN
T GGT AAT CTG ACC TGG GTG CCC AAC GGT GCC CCC GAG GCA GCC CTG TCA AAC ACC AGC AA
        2110            2120            2130            2140            2150            2160

PRO THR ALA TYR ASN LYS ALA PRO PHE THR ARG LEU ALA LEU PRO TYR THR ALA PRO HIS
```

FIG. 13c CONTINUED

```
VAL THR ARG ALA ASP ASP THR ARG LEU LEU ALA LYS PHE ASP VAL SER LEU ALA ALA LYS
CGTTACGCGGGCAGACGACACCCGTCTTTTGGCCAAGTTTGATGTCTCCCTTGCCGCAAAA
        1390              1400              1410              1420              1430              1440

HIS MET SER ASN THR TYR LEU SER GLY ILE ALA GLN TYR TYR THR GLN TYR SER GLY THR
ACACATGTCCAACACATACCTATCAGGGATTGCACAGTACTACACACAGTACTCTGGTAC
        1450              1460              1470              1480              1490              1500

ILE ASN LEU HIS PHE MET PHE THR GLY SER THR ASP SER LYS ALA ARG TYR MET VAL ALA
TATCAACCTGCACTTCATGTTCACAGGCTCCACTGACTCCAAAAGCCGCTACATGGTGGC
        1510              1520              1530              1540              1550              1560

TYR ILE PRO LEU GLY VAL GLU THR PRO PRO ASP THR PRO GLU GLU ALA ALA HIS CYS ILE
TTACATCCCGCTCGGGGTCGAGACACCGCCGGACACACCTGAAGAAGCTGCTCACTGCAT
        1570              1580              1590              1600              1610              1620

HIS ALA GLU TRP ASP THR GLY LEU ASN SER LYS PHE THR PHE SER ILE PRO TYR VAL SER
TCACGCTGAGTGGGACACAGGACTGAACTCCAAATTCACCTTTTCAATCCCCTTACGTGTC
        1630              1640              1650              1660              1670              1680

ALA ALA ASP TYR ALA TYR THR ALA SER ASP THR ALA GLU THR THR ASN VAL GLN GLY TRP
TGCCGCGGATTACGCGTATACCGCATCTGATACGGCAGAGACAACAAATGTACAGGGATG
        1690              1700              1710              1720              1730              1740

VAL CYS VAL TYR GLN ILE THR HIS GLY LYS ALA GLU ASN ASP THR LEU LEU VAL SER ALA
GGTCTGTGTTTACCAAATTACACACGGGAAGGCTGAAAATGACACCTTGTTAGTGTCGGC
        1750              1760              1770              1780              1790              1800
                                                                                          VP3│VP1
SER ALA GLY LYS ASP PHE GLU LEU ARG LEU PRO ILE ASP PRO ARG THR │THR THR THR
TAGCGCCGGCAAAGACTTTGAGTTGCGCCTCCCAATTGACCCCCGGACACAA ACCACTAC
        1810              1820              1830              1840              1850              1860
```

FIG. 13c

```
VAL ALA MET VAL PRO GLU TRP LYS ALA PHE ASP THR ARG GLU LYS TYR GLN LEU THR LEU
GGT GGC CAT GGT GCC AGA GTG GAA GGC ATT TGA CAC ACG TGA AAA TAC CAG CTT ACC CT
            910               920               930               940               950               960

PHE PRO HIS GLN PHE ILE SER PRO ARG THR ASN MET THR ALA HIS ILE THR VAL PRO TYR
TTT CCC ACA CCA GTT TAT TAG CCC CAG AAC TAA CAT GAC TGC CCA CAT CAC GGT ACC GTA
            970               980               990              1000              1010              1020

LEU GLY VAL ASN ARG TYR ASP GLN TYR LYS LYS HIS LYS PRO TRP THR LEU VAL VAL MET
TCT TGG TGT GAA CAG GTA CGA TCA GTA CAA GAA ACA CAA ACC TTG GAC ACT GGT TGT CAT
           1030              1040              1050              1060              1070              1080

VAL LEU SER PRO LEU THR VAL SER ASN THR ALA ALA PRO GLN ILE LYS VAL TYR ALA ASN
GGT ACT ATC ACC CCT CAC GGT TCA GCA ACA CTG CCG CCC ACA AAT CAA GGT CTA CGC CAA
           1090              1100              1110              1120              1130              1140
                                                                            VP2 VP3
ILE ALA PRO THR TYR VAL HIS VAL ALA GLY GLU LEU VAL THR PRO SER LYS GLU GLY ILE PHE PRO
CAT TGC CCC AAC CTA CGT TCA CGT GGC TGG AGA GCT TGT GAC ATT CCC TCG AAA GAG GGG ATT TTC CC
           1150              1160              1170              1180              1190              1200

VAL ALA CYS ALA ASP GLY TYR GLY LEU PRO PRO LYS THR ASP THR ASP PRO LYS THR ALA ASP PRO
AGT TGC ATG CGC AGA CGG TTA CGG AGG ACT GGT GAC AAC AGA CCC GAA AAC AGC TGA CCC
           1210              1220              1230              1240              1250              1260

VAL TYR GLY LYS VAL TYR ASN PRO PRO LYS THR ASN TYR PRO GLY ARG PHE THR ASN LEU
TGT TTA CGG TAA GGT GTA TAA CCC GCC AAG ACC AAC TAC CCC GGG CGC TTT ACA AAC CT
           1270              1280              1290              1300              1310              1320

LEU ASP VAL ALA GLU ALA CYS PRO THR PHE LEU ARG PHE ASP ASP GLY LYS PRO TYR VAL
ATT GGA CGT GGC CGA AGC ATG TCC CAC CTT TCT TCG TTT CGA CGA TGG GAA ACC GTA CGT
           1330              1340              1350              1360              1370              1380
```

FIG. 13b CONTINUED

```
THR SER THR THR GLN SER SER VAL GLY VAL THR TYR GLY TYR SER THR GLU GLU ASP HIS
CACTTCGACCACCCAGTCGAGTGGGAGTCACGTATGGGTACTCCACTGAGGAAGATCA
         610                620                630                640                650                660

VAL ALA GLY PRO ASN THR SER GLY LEU GLU THR ARG VAL VAL GLN ALA GLU ARG PHE PHE
CGTTGCTGGGCCCAACACATCGGGCTTAGAGACGCGGGTGCAGGCAGAGAGATTTTT
         670                680                690                700                710                720

LYS LYS PHE LEU PHE ASP TRP THR THR ASP LYS PRO PHE GLY TYR LEU THR LYS LEU GLU
CAAGAAGTTTCTGTTTGACTGGACAACGGACAAACCTTTTGGATACTTGACAAAACTGGA
         730                740                750                760                770                780

LEU PRO THR ASP HIS HIS GLY VAL PHE GLY VAL HIS LEU VAL ASP SER TYR ALA TYR MET ARG
GCTTCCCACCGATCACCACGGTGTCTTCGGGCACTTGGTGGACTCATATGCATATGAG
         790                800                810                820                830                840

ASN GLY TRP ASP VAL GLU VAL CYS ALA VAL GLY ASN GLN PHE ASN GLY GLY CYS LEU LEU
GAACGGGCTGGGATGTTGAGGTATGTGCCGTCGGCAACCAGTTCAACGGCGGGTGCCTTCT
         850                860                870                880                890                900
```

```
        E  PLAC                              E
          ←                          P
      P       H                          pFA  61/t 76
         pXY 1                              6·8 Kb
         4·1 Kb
                                                      P
         ① Eco RI, Pst
            double digest
         ② Isolate 3·4 Kb          ③ Eco RI total
            fragment                  Pst Partial
                                      digest
                          ⑤ Ligate   ④ Isolate 3·9 Kb
                          ⑥ Transform Ecoli  fragment
                          ⑦ Screen for Tc resistance
                             confirm contruction by
                             restriction mapping E  PLAC
                      ←    H
                P
                     pWRL 1000
                       7·3 Kb
         FMDV
         coding                          P
         sequence
                           →
```

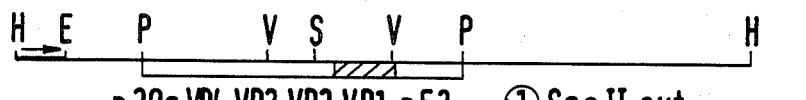
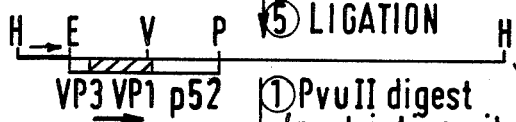
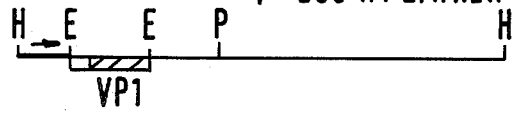
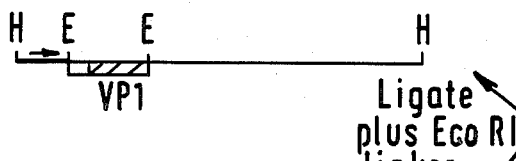
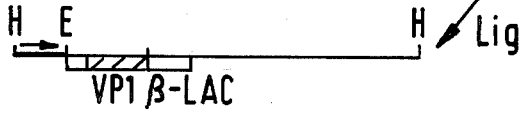
FIG. 16

FIG.17

| | | | SIZE OF PROTEINS | |
|---|---|---|---|---|
| | | | NO. OF AMINO ACIDS | MOLEC WT. |
| pWRL 1104 | VP3 VP1 212αα | p52 ~230αα +? | ≥490 | ≥54K |
| pWRL 1120 | VP3 VP1 210αα | ↑4αα | 260 | 29K |
| pWRL 1130 | VP3 VP1 210αα | ↑12αα | 270 | 30K |
| pWRL 1140 | VP3 VP1 210αα | β-lac ← 104αα (C-TERMINAL) | 360 | 40K |

↑~40αα
10αα β-Galactosidase
(N-TERMINAL)

FIG.18

① pWRL 1004

After translating the FMDV p52 sequences the ribosome will encounter a poly C (proline) sequence and terminate after 11, 32 or 106 amino acids depending on the reading frame.

② pWRL 1120      EcoRI LINKER

```
    ---   CAG | GGA  ATT  CCC  TGT ‖ TGA
          Gln | Gly  Ile  Pro  Cys ‖ STOP
       ↑
  VP1 aa₂₁₀         (OUT-OF-FRAME FMDV SEQUENCE)
```

③ pWRL 1130     (OUT-OF-FRAME IN β-LACTAMASE)

```
    ---   CAG | GGA  ATT  CCG  CAA  TGG  Cont.
          Gln | Gly  Ile  Pro  Gln  Trp  —
  VP1 aa₂₁₀

-CAA  CAA  CGT  TGC  GCA  AAC  TAT ‖ TAA
  -Gln  Gln  Arg  Cys  Ala  Asn  Tyr ‖ STOP
```

④ pWRL 1140    (IN-FRAME WITH β-LACTAMASE)

```
  GCA  AAA  CAG | GCA  ATG  GCA  ---  CAT  TGG ‖ TAA
  Ala  Lys  Gln | Ala  Met  Ala  ---  His  Trp ‖ STOP
              ↑     ↑                       ↑
       VP1 aa₂₁₀   β-LACTAMASE        β-LACTAMASE
                     aa₁₈₃                aa₂₈₆
```

FIG.19

GACTCGCCGTTCCACTCTGGACCAGACGAGTACCGGCGCTCTTT<u>GAG</u>CCC
                                             1
TTC<u>TAG</u>GGCTCTTT<u>TGA</u>GATCCCAAGCTACAGATCACTTTACCTGCGTTGGG
   2          3
<u>TGA</u>ACGCCGTGTGCGG<u>TGA</u>CGCA<u>TAA</u>TCCCCAGAGATCAGAATTGGCACT
 2              3      1
TCGGCTCTGGGGCGCGCGACGCCGT<u>TAGGAGTGA</u>AAAGCTCGA...(A)$_{20}$
                         3    3

$\overline{1}$ )
$\overline{2}$ )    Stop codons in three reading phases
$\overline{3}$ )

...    Sequence unclear

RECOMBINANT DNA EXPRESSION VECTOR ENCODING FOR FOOT AND MOUTH DISEASE VIRUS PROTEINS

This application is a continuation of application Ser. No. 299,884, filed Sept. 8, 1981.

This invention relates to DNA molecules comprising artificially constructed polynucleotide sequences substantially corresponding to all or a portion of foot and mouth disease RNA, in particular it relates to polynucleotide sequences coding for at least one protein. It especially relates to DNA molecules comprising artificially constructed polynucleotide sequences coding for the whole or part of one or more proteins occurring in foot and mouth disease virus (hereinafter referred to as FMDV), or its precursor or a modification thereof. Such DNA molecules are capable of being expressed as a polypeptide(s).

Foot and mouth disease (FMD) is one of the most virulent and contagious diseases of farm animals. The disease is endemic in several areas of the world and can be found in many countries of Africa, Asia and South America where it is controlled to varying degrees by immunisation programmes. Countries which are free of the disease remain so only by strict import and quarantine controls, together with the use of slaughter when outbreaks occur.

FMDV is an RNA (ribonucleic acid) virus classified as a member of the genus Apthovirus of the family Picornaviridae (see Cooper, P. D., et al, *Intervirology*, 10, 165–180, 1978). There are seven known serotypes of FMDV, the European serotypes, A, O and C, the South Africa Territories serotypes SAT 1, SAT 2 and SAT 3, and the Asia 1 serotype. A number of antigenically distinct subtypes are recognised within each of these serotypes, and as the subtypes are so distinct immunologically specific subtype vaccines are required. For each serotype or subtype several genetically distinct variants exist.

Foot and mouth disease virus comprises a single strand of RNA and four major polypeptides, namely $VP_1$, $VP_2$, $VP_3$ and $VP_4$, which form the capsid proteins of the virus. The protein referred to here as $VP_1$ is variously referred to by other workers in the field as $VP_3$, $VP_{Thr}$ and $VP_T$ (see Bachrach, H. L. et al, *J. Immunology*, 115, 1636–1641, 1975; Strohmaier, K. et al. *Biochem. Biophys. Res. Comm.*, 85, 1640–1645, 1978; Bachrach, H. L. et al, *Intervirology*, 12, 65–72, 1979). Each of the polypeptides $VP_1$, $VP_2$, and $VP_3$ has a molecular weight of about 26,000, whilst $VP_4$ has a molecular weight of about 8,000 and it is generally considered that there are approximately 60 copies of each of them in the virus. The other polypeptides translated from the virus RNA probably have a role in virus replication.

The single strand of FMDV RNA has a molecular weight of about $2.6 \times 10^6$ which is equivalent to about 8000 nucleotides, and is of positive polarity acting as a template for both translation into polypeptides and RNA synthesis. One of the primary translational products is a protein designated P88 which is subsequently cleaved to produce the four capsid proteins $VP_1$ to $VP_4$.

Capsid protein $VP_1$, mentioned above, is susceptible to cleavage when intact virus is treated with trypsin, resulting in a large decrease in infectivity of most strains of FMDV (Wild, T. F. and Brown, F., *J. Gen. Virology*, 1, 247–250, 1967). Trypsin treatment may also reduce the capacity of virus to stimulate the production of neutralising antibody. Thus it appears that $VP_1$, is likely to be the primary immunogen capable of eliciting effective protection against infection by FMDV and indeed $VP_1$ separated from virus particles produces neutralising antibody and elicits effective protection against the virus (Laporte, J. et al, *C. R. Acad. Sc. Paris*, t. 276 Serie D, 3399–3401, 1973; Bachrach, H. L. et al, *J. Immunology*, 115, 1636–1641, 1975.). Separation of the naturally occurring FMDV capsid proteins, particularly $VP_1$, in order to provide a safer vaccine has necessitated the use of strongly denaturing conditions and is generally held by those skilled in the art to be disadvantageous for the maintenance of optimum immunogenicity and production of an effective vaccine.

Using the techniques developed over the last five years it is now possible to introduce the DNA (deoxyribonucleic acid) coding for non-bacterial proteins into bacterial cells via the intermediary of a plasmid or other cloning vehicle, (see for example Burrell, C. J, et al, *Nature*, 279, 43–47, 1979.). In general the construction of the recombinant DNA molecules comprises the steps of deriving the DNA template coding for the desired protein from the non-bacterial parent and inserting this piece of heterologous DNA into a cloning vehicle, such as a bacterial plasmid, and then transforming an appropriate bacterial host with the modified plasmid. A general discussion of the manipulation of genes leading to the formation of recombinant DNA was published by S. Cohen in *Scientific American*, 233, 24–33, 1975.

Several non-bacterial genes have been inserted and multiplied within bacteria such as *Escherichia coli*, and several non-bacterial proteins have been expressed by bacteria using recombinant DNA technology, including the haemagglutinin of influenza viruses (Porter, A. G. et al, *Nature*, 282, 471–477, 1979) and the hepatitis B virus protein (Burrell, C. J et al, 1979, loc. cit.). Notwithstanding the considerable amount of work carried out in recent years on recombinant DNA research, there has been a considerable dearth of results amenable to immediate and practical application, especially in the field of recombinant DNA involving the manipulation of viral genetic material.

The present invention represents the first disclosure of the synthesis of individual polypeptides substantially equivalent to naturally occurring picornavirus capsid proteins, in particular FMDV capsid proteins, and also for the serial synthesis of several FMDV polypeptides either as individual entities or as fusion products of parts of two or more proteins. In addition, the present invention provides the means for the concurrent synthesis of immunogenic proteins normally encoded for by different variants of FMDV, without the numerous hazards associated with the culture of FMDV.

According to one aspect of the present invention there is provided a DNA molecule comprising a nucleotide sequence substantially corresponding to all or a portion of FMDV RNA or biologically functional fragments thereof, as hereinafter defined. Preferably nucleotide sequence codes for at least one polypeptide of foot and mouth disease virus. Such a DNA molecule is capable of being expressed as a polypeptide recognisable as substantially corresponding to a FMDV protein. Preferably the nucleotide sequence codes for a structural protein of FMDV such as $VP_1$ or alternatively it may code for all of the structural or capsid proteins contiguously enabling them to be synthesised as one precursor, for example as P88 which may require stabilisation by inhibitors of the enzymes such as proteases which break it down to its constituent proteins. Alternatively the nucleotide sequence may code for $VP_1$ contiguous with the whole or part of any one of proteins $VP_2$, $VP_3$ and $VP_4$, in particular the sequence codes for $VP_1$ alone or together with the whole or part of $VP_3$. In yet another alternative the nucleotide sequence may code for all or a portion of at least two FMDV proteins each one derived from a different variant of FMDV.

In a preferred aspect the nucleotide sequence codes for a protein of FMDV serotype A or O, most preferably serotype A10 and in particular strain 61. Furthermore the nucleotide sequence may have control sequences positioned adjacent to it, such control sequences being derived either from FMDV nucleic acid or from a heterologous source.

In another aspect of the present invention there is provided a recombinant DNA molecule comprising an operon having initiator sequences and terminator sequences as hereinafter defined, and a nucleotide sequence substantially coding for all or part of at least one protein of foot and mouth disease virus, the nucleotide sequence being located between the initiator sequences and terminator sequences of the operon.

The invention also provides a recombinant DNA cloning vehicle capable of expressing all or part of a protein of FMDV comprising an operon having initiator sequences and terminator sequences, and a nucleotide sequence substantially coding for all or part of at least one portion of foot and mouth disease virus, the nucleotide sequence being located between the initiator sequences and terminator sequences of the operon.

In a further aspect of the invention there is provided a host cell containing a recombinant DNA cloning vehicle and/or a recombinant DNA molecule as defined above.

The invention also comprises an antigen for stimulating the production of antibodies against FMDV in a mammal comprising at least one polypeptide displaying FMDV immunogenicity prepared by the expression of a DNA molecule as hereinbefore defined and produced by a host cell transformed with a recombinant DNA cloning vehicle as hereinbefore defined and produced by a host cell transformed with a recombinant DNA cloning vehicle as hereinbefore defined.

The invention further provides a method of preparing a DNA molecule substantially coding for at least one polypeptide of FMDV comprising:
(a) isolating FMDV single stranded RNA;
(b) preparing a first single strand of DNA complementary to the single strand of FMDV RNA;
(c) preparing a second single strand of DNA complementary to and hydrogen bonded to the first DNA strand so as to produce a double strand of DNA.

The double strand of DNA so produced can be inserted into a cloning vehicle following digestion of the cloning vehicle with a restriction endonuclease, free ends of the cloning vehicle being joined to the DNA molecule so as to form a recombinant cloning vehicle. This in turn can be inserted into a suitable host cell by for example transformation.

As used herein the terms listed below have the following meanings:

Nucleotide: a unit of DNA or RNA comprising a sugar moiety (pentose), a phosphate and a nitrogenous heterocyclic base. The base is joined to the sugar moiety via the glycosidic carbon (1' carbon of the pentose) and the base characterizes the nucleotide. The four DNA bases are adenine (A), guanine (G), cytosine (C) and thymine (T). The four RNA bases are A, G, C and uracil (U).

Recombinant DNA: a hybrid double stranded DNA sequence comprising at least two double stranded DNA nucleotide sequences, the first sequence not being found together in nature with the second sequence.

Cloning Vehicle: non-chromosomal double stranded DNA capable of replicating when placed within a unicellular micro-organism.

Plasmid: a cloning vehicle derived from viruses or bacteria.

Structural Gene: a sequence of DNA nucleotides which codes for a sequence of amino acids characteristic of a specific polypeptide.

Initiator Sequences: sequences of DNA nucleotides which control the initiation of transcription or translation.

Terminator Sequences: sequences of DNA nucleotides at which transcription or translation ceases.

Transcription: the process whereby RNA polymerase is caused to move along the DNA sequence forming messenger RNA.

Translation: the process of producing a polypeptide from messenger RNA.

Operon: a structural gene(s) coding for polypeptide expression which is preceded by initiator sequences and succeeded by terminator sequences.

Expression: the process involved in producing a polypeptide from a structural gene.

Biologically functional fragment: a DNA molecule which codes for antigenic determinants capable of eliciting an immune response in a mammal, or codes for a protein or part of a protein which is required for the appropriate conformation of an antigenic determinant, or codes for a protein or part thereof which is important in the life cycle of FMDV in vivo and/or in vitro.

The invention will be further described by way of reference to the accompanying drawings in which:

FIGS. 4 to 7 are diagrams of the DNA and amino acid sequences indicated by thick lines in FIG. 3.

FIG. 8 is a diagram comparing the $VP_1$ N-terminal amino acid sequences from five strains of FMDV.

FIG. 9 is a diagram of C-terminal nucleotide sequence of $VP_3$ and the N-terminal nucleotide sequence of $VP_1$ in recombinant plasmid pFA61/t76.

FIG. 10 is a diagram of the nucleotide and amino acid sequences at the junction of the region coding for $VP_2$ and $VP_3$ in recombinant plasmid pFA61/t76 which follows directly from the sequencing in FIG. 5.

Figure 12A:
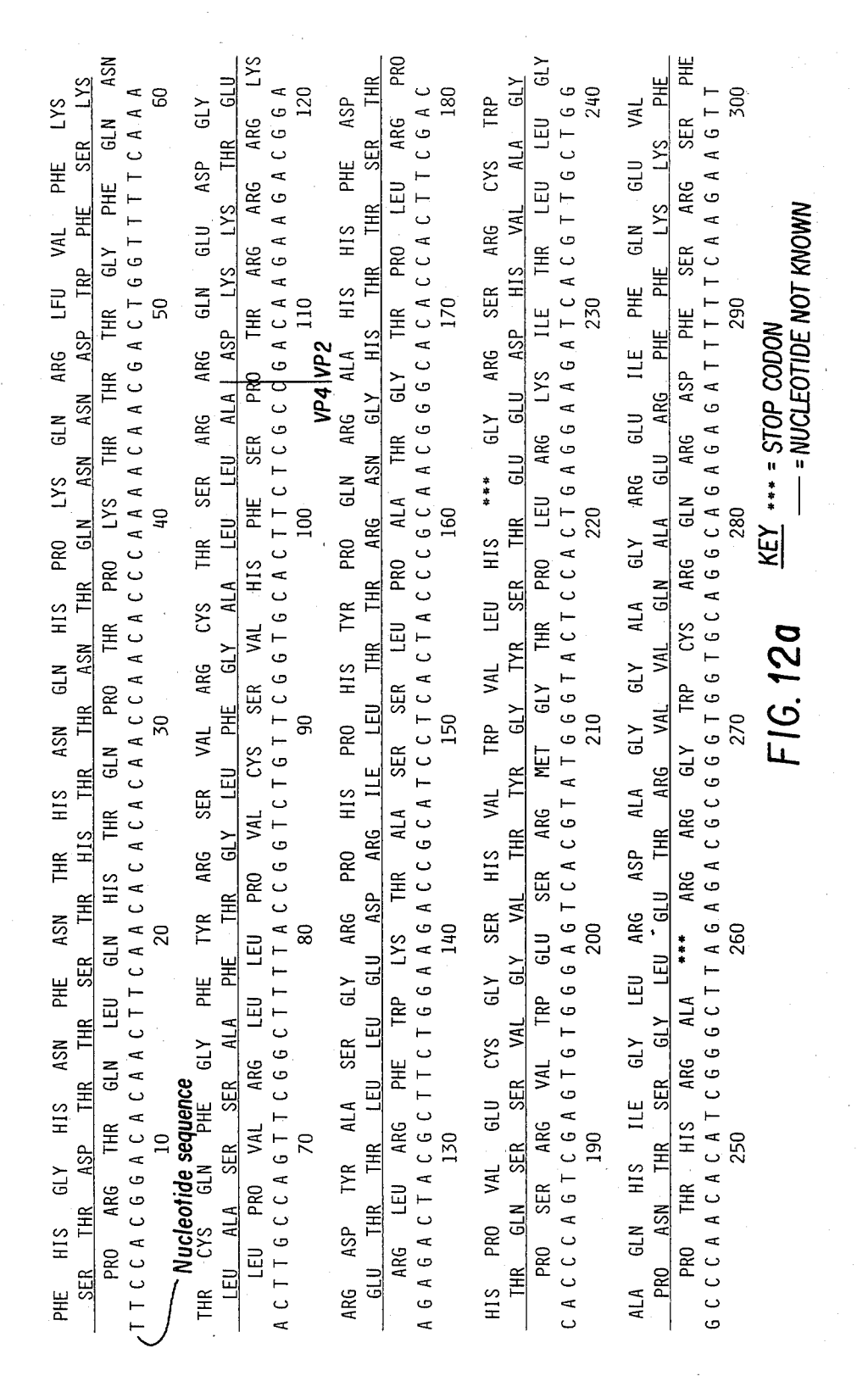
Figure 12C:
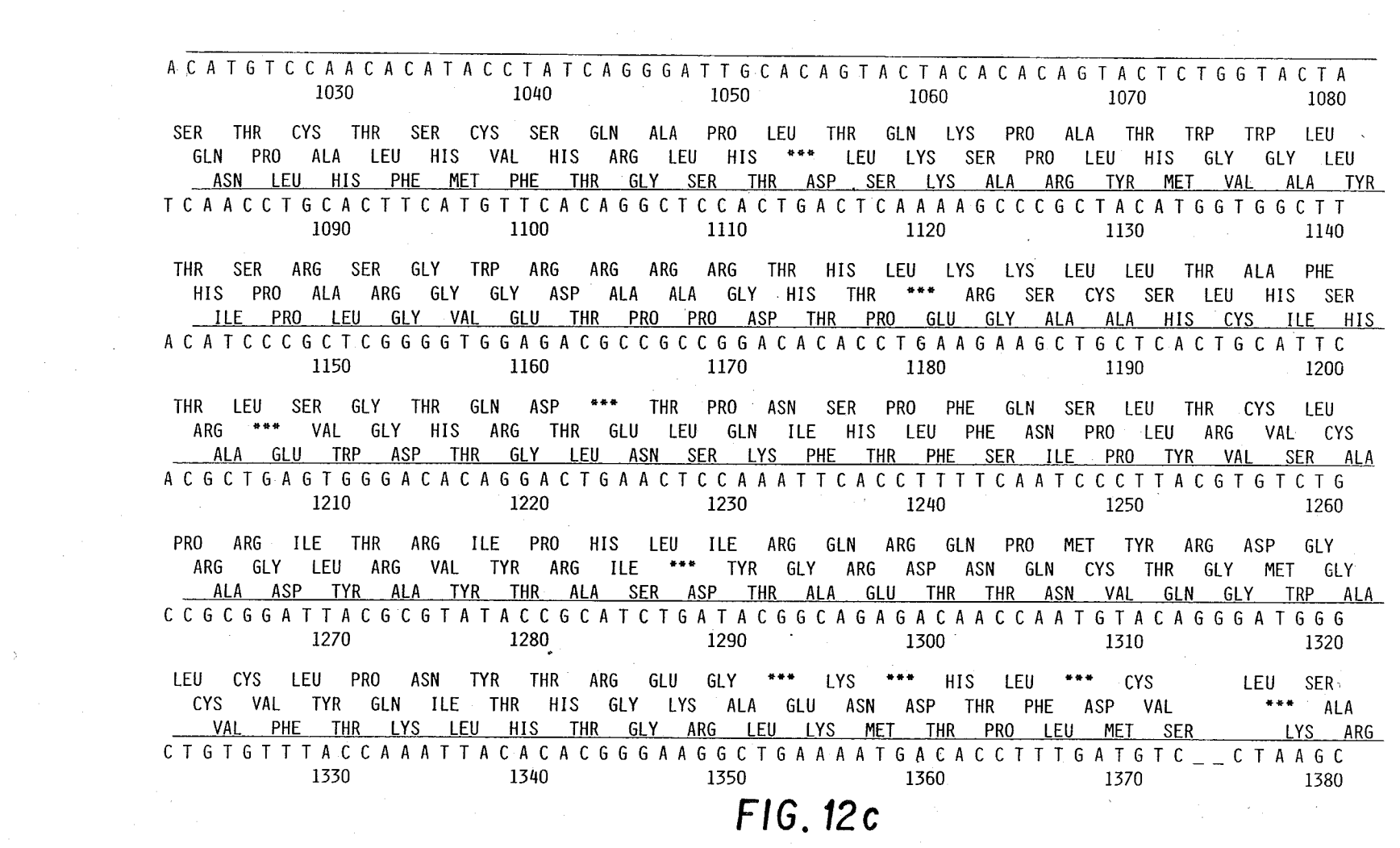

FIG. 12 is a diagram of the DNA sequence and predicted amino acid sequence of the FMDV structural gene region inserted into recombinant plasmid pFA A61/t76.

FIG. 13 is a diagram of the DNA sequence and predicted amino acid sequence of $VP_4$, $VP_2$, $VP_3$ and $VP_1$ inserted into recombinant plasmid pFA A61/t76.

FIG. 15 is a schematic diagram of the introduction of FMDV ds cDNA into plasmid pXY1.

FIG. 16 illustrates the construction of expression plasmids.

FIG. 17 illustrates the protein products and molecular weights of the proteins produced by the expression of the plasmids shown in FIG. 16.

FIG. 18 illustrates the C-terminal nucleotide and amino acid sequences of the proteins shown in FIG. 17.

FIG. 19 is a diagram of the nucleotide sequence of PFA61/t243 corresponding to the 3' end of FMDV RNA including at least part of the poly A tail.

Figure 1:
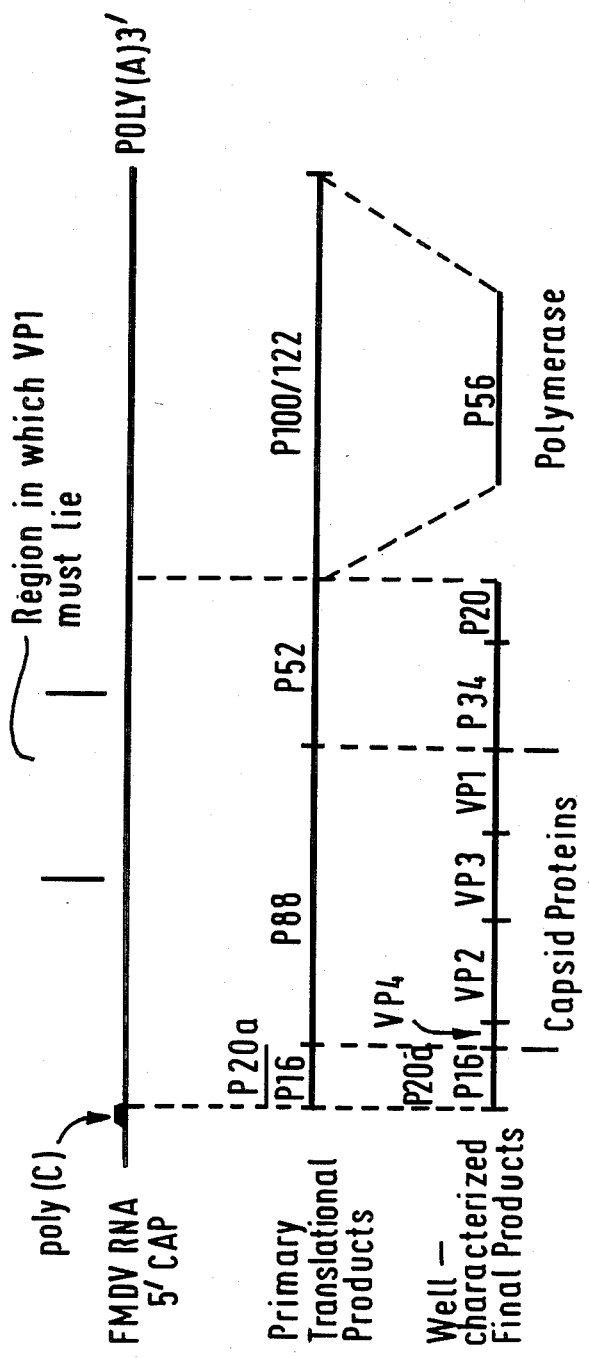
FIG. 1 is a schematic diagram of the genetic map of FMDV RNA and the proteins derived therefrom.

Referring to FIG. 1, this shows a simplified map of FMDV RNA, which, as stated previously, is about 8000 nucleotides long. Translation of the RNA is from the 5' to 3' end. As with many messenger RNA molecules, FMDV RNA contains a polyadenylic acid sequence at the 3' end. It contains in addition a polycytidylic acid tract of about 100–200 nucleotides in length, depending on the strain of virus. The polycytidylic acid tract is located about 400 nucleotides from the 5' end of the RNA (Rowlands, D J et al, *J. Virology*, 26, 335–343, 1978).

FMDV RNA is translated as a polyprotein which is cleaved during translation to give several large polypeptides referred to as primary products designated by "P" and a number. These primary products are then cleaved, probably by virus coded proteases into ultimate polypeptide products such as $VP_1$. There are portions of FMDV RNA which do not code for a protein but which play an important part in the life cycle of FMDV in vitro and/or in vivo, for example they affect the viability of the virus.

From the study of kinetics of translation of viral information into polypeptides in both virus infected cells and cell-free protein synthesising systems, the order on the viral genome of the genetic information encoding the major polypeptides has been deduced. (Doel, T. R. et al, *J. Gen. Viral.*, 4, 395–404, 1978; Sanger, D. V. et al, *J. Virol*, 33, 59–68, 1980). From these studies it has been found that the first 550 nucleotides of FMDV RNA, from the 5' end, do not appear to code for any polypeptide. Proteins P16 and P20a are closely related and contain the initiation site of FMDV translation as shown by exclusive labelling with N-formyl methionine during in vitro analysis (Sanger, D. V. et al, 1980 loc. cit.). P88 is the primary product which is split up into $VP_{1-4}$. From an evaluation of the prior art the gene for $VP_1$ is approximately 700 nucleotides and must lie within the region bounded by nucleotide positions 2300 and 3800.

A variety of techniques are available for preparing the recombinant DNA molecule according to the invention, one of which comprises the steps of synthesising a single stranded DNA copy (cDNA) of the RNA purified from an isolate of whole, virulent FMDV, using a reverse transcriptase enzyme. After the original RNA strand has been degraded the cDNA is converted into a double strand (ds cDNA), which is then treated to remove any loops of DNA which have formed using, for example, a nuclease enzyme. An alternative method of preparing the double stranded cDNA is via chemical synthesis using techniques well known in the art.

Once the double stranded cDNA has been produced the next step is to insert it into a cloning vehicle, which may be for example a bacterial plasmid or bacteriophage. This may be achieved by first cleaving the DNA of the purified cloning vehicle using a restriction endonuclease enzyme such as Pst 1, which cleaves the DNA at sites where complementary nucleotides are arranged in rotational symmetry. The double stranded FMDV ds cDNA can then be inserted between and linked to the open ends of the cloning vehicle by one of several methods. For example several "G" nucleotides can be attached to the 3' end of the cloning vehicle by a process called homopolymer tailing, which involves the use of a terminal transferase enzyme. In a similar fashion several "C" nucleotides are added to the 3' end of the double stranded FMDV cDNA. The tailed cloning vehicle and double stranded cDNA are then mixed together where upon the cohesive termini formed by the tailing anneal together.

There are several alternatives to 'tailing'. One involves digestion of ds cDNA with endonucleases forming either blunt or cohesive termini. Blunt termini may be made cohesive by exonuclease digestion. In another method, blunt ends may be directly joined using a DNA ligase enzyme. In yet another method, synthetic oligonucleotides may be joined to blunt ended ds cDNA and the new termini made cohesive by either exonuclease or endonuclease digestion, prior to ligation with appropriately linearized cloning vehicle.

Once the double stranded FMDV cDNA has been annealed with the DNA of the cloning vehicle, an appropriate host, such as a bacterium, is transformed with the recombinant cloning vehicle, so as to permit that host to express the FMDV ds cDNA, and thereby produce a polypeptide or polypeptides displaying FMDV antigenicity.

There are several host-cloning vehicle combinations that could be used for the expression of FMDV proteins. For example useful cloning vehicles include bacterial plasmids such as pAT 153, (Twigg, A. J. *Nature*, 283, 216–218, 1980; obtainable from Prof. D. Sherratt, University of Glasgow, Scotland.), pBR 322, (Sutcliffe, J. G. Cold Spring Harbour Symposium for Quantitative Biology, 43, 77–90, 1978; obtainable from Dr. H. Boyer, University of San Francisco, U.S.A.), other *E. coli* plasmids and wider host range plasmids. Bacteriophages such as the many derivatives of phage λ may also be suitable. Hosts that may be used include bacteria such as strains of *E. coli* K. 12, e.g. *E. coli* HB101, (Boyer, H. W. et al, *J. Mol. Biol.*, 41, 459–472, 1969; obtainable from Dr. H. Boyer, University of San Francisco, U.S.A.), *E. coli* χ1776, (Curtiss, R. et al. Ann Report Dept. of Microbiology, University of Alabama, 1976, 96–106; obtainable from Dr. R. Curtiss III, University of Alabama, Birmingham, USA), *E. coli* χ2282 (obtainable from Dr. R. Curtiss III) and *E. coli* MRC1, (obtainable from Dr. S. Bremer, University of Cambridge, England), strains of *Bacillus subtilis* and Pseudomonas, as well as yeasts and other fungi, and other unicellular organisms. It is only to be expected, however, that not all hosts will be equally effective Within each cloning vehicle, various sites may be available for insertion of the FMDV ds cDNA, each site being designated by the restriction endonuclease enzyme which cleaves the DNA. Thus, for example, enzyme Pst 1 cleaves plasmid pAT 153 in the gene coding for penicillin resistance. There are several other endonuclease enzymes that can be employed including Hind III and Eco RI.

The selection of the site on the cloning vehicle for insertion of FMDV ds cDNA may be governed by a variety of factors, for example size of polypeptide to be expressed and location of initiator and terminator sequences. Consequently not all sites may be equally effective for a given polypeptide. Selection of the site may also be governed by the initial screening method employed for detecting recombinants, for example as stated Pst 1 cleaves plasmid pAT 153 in the gene coding for ampicillin resistance, thus colonies of transformants displaying tetracycline resistance but ampicillin sensitivity are likely to contain at least some FMDV ds cDNA.

It is essential that the FMDV ds cDNA inserted into the cloning vehicle can be read in the correct phase. In order to achieve this it may be necessary to insert supplementary nucleotides for example between the starting points of transcription and translation of the FMDV ds cDNA fragment whose expression is desired. Addition of such nucleotides must not, of course, form a nucleotide sequence that could interrupt translation.

Expression of FMDV ds cDNA, which has been inserted into a cloning vehicle, which in turn has been used to transform a suitable host cell, may be detected by the appearance of a function specific for the protein, that is immunological activity in the case of FMDV. Several methods are available, for example the essentially immunological colony screening method disclosed by S. Broome and W. Gilbert in *Proc. Nat. Acad. Sci.*, 1978, 75, 2746–2749. One alternative, and somewhat simpler technique, is to inject into a laboratory animal the crude bacterial derived from a culture of bacteria transformed with an appropriately engineered cloning vehicle and to test for the formation of appropriate antibodies. A second alternative is to perform an immunoprecipitation of a crude extract of the bacterial cells. Yet a further method is the "Maxicell Technique" described by Sancar et al in *J. Bact.*, 1979, 137, 692–693.

The nature of the polypeptide produced as a result of expression by the host of the recombinant DNA molecule of the invention will depend on the point of insertion into the DNA of the cloning vehicle, so that in practice a precursor polypeptide may be formed which comprises a polypeptide coded for by FMDV ds cDNA and an additional polypeptide coded for by the DNA of the cloning vehicle. Thus, for example, if the plasmid pAT 153 is cleaved by Pst 1 a precursor polypeptide comprising a portion of the penicillinase enzyme and the polypeptide coded for by the FMDV ds cDNA may be expressed. The precursor polypeptide may then be selectively cleaved so as to separate the desired FMDV polypeptide from the superfluous amino acid sequence. Usually cleavage will be effected outside the host following harvest of the microbial culture by techniques well known to those skilled in the art. Cleavage may be necessary in order that the FMDV expression product can exert the desired activity, however during harvest of the microbial culture the fact that a superfluous amino acid sequence is linked to the required FMDV polypeptide may help to prevent degradation of the expression product by endogenous enzymes. Alternatively cleavage may be effected within the host, this may be achieved by inserting into the cloning vehicle, DNA coding for the desired cleavage enzymes.

The production of a fusion product of a polypeptide coded for by FMDV ds cDNA and a portion of for example penicillinase enzyme may increase the stability of the hybrid protein in *E. coli* and even enhance the immunogenicity of the FMDV protein.

Alternatively, appropriate nucleotide sequences, derived for example from FMDV RNA, may be inserted before the FMDV ds cDNA so as to ensure that the FMDV ds cDNA can be expressed alone, and not as a fusion product with a host polypeptide.

Once transformants containing at least some of FMDV ds cDNA have been identified, as explained above, the recombinant cloning vehicle DNA is purified and then analysed in order to determine how much of the FMDV ds cDNA has been inserted. In order to do this the recombinant cloning vehicle DNA is treated with several different restriction endonucleases, for example Eco RI, Pst 1, Sal 1, Bgl II, Bam H1, Hind III and Hinf 1, and the digestion products may be analysed by gel electrophoresis. Using these results, together will those obtained when T1 oligonucleotides, produced by RNase digestion of FMDV RNA by T1 nuclease, are allowed to hydridize with separated restriction endonuclease digestion products of the recombinant DNA, maps of the FMDV ds cDNA inserted into the cloning vehicle, similar to those shown in FIG. 2, may be produced. From such maps it is possible to select the recombinant that contains the desired FMDV gene, for example the gene coding for $VP_1$.

In another aspect of the invention there is provided a method of mapping the recombinant DNA molecule as hereinbefore defined comprising:
(a) digesting the DNA with restriction endonuclease enzymes and separating the products;
(b) adding labelled olignucleotides of FMDV RNA produced by $T_1$ ribonuclease digestion;
(c) identifying the products of restriction endonuclease digestion to which the $T_1$ oligonucleotides have hybridlized.

The various DNA molecules may be useful as a probe for the in vitro diagnosis of the presence in biological samples of FMDV, and in particular may be used to determine the serotype or subtype causing an outbreak of FMD. For this purpose the DNA molecules may be labelled, in known manner, with a radioactive isotope. In addition the expression product of the recombinant cloning vehicle may be used for serological diagnosis and in the preparation of single or multivalent vaccines against FMD, by methods well known in the art of vaccine manufacture. Such vaccines are effective in stimulating antibodies in vaccinated animals and thereby protecting against FMD.

In another aspect of the invention there is provided a vaccine for stimulating the production of antibodies against FMDV in a mammal comprising at least one protein displaying FMDV immunogenicity produced by a host cell as hereinbefore defined together with a veterinarily acceptable carrier therefor.

In yet a further aspect of the invention there is provided a method of stimulating the production of antibodies against FMDV in a mammal, comprising administering an immunologically effective non-toxic amount of a vaccine as defined above. The term "immunologically effective non-toxic amount" is used to denote an amount of protein displaying FMDV immunogenicity sufficient to stimulate enough antibodies in a mammal, such that if the mammal encounters virulent FMDV, following vaccination, it does not succomb to the disease, and which is not toxic to the mammal.

Further characteristics and features of the invention are described in the following Examples which are presented by way of illustration only and are not to be considered as limiting the scope of the present invention in any way.

EXAMPLE 1

Preparation of FMDV RNA

Approximately 10 ml of a recent harvest of FMDV type A10 (strain A61) (freely available on application to Animal Virus Research Institute, Pirbright, England, subject to the requirements of the law of individual countries) in Eagle's medium were added to each of ten Roux bottles containing monolayers of approximately $10^8$ $BHK_{21}$ cells. After gentle shaking for 30 min the medium was decanted and 20 ml fresh medium added to each bottle. After the virus infection had destroyed the cell monolayers (3–4 h), the medium was decanted and the cell debris was removed by centrifugation at 12,000 xg for 15 min at 4° C. The virus was then pelleted by spinning at 90,000 xg for 1 hr at 4° C. The virus pellet was resuspended in 2 ml of TNE buffer (10 mM Tris-HCl (pH 7.5) 150 mM NaCl and 1 mM EDTA (ethylenediamino tetracetic acid) and the suspension was cleared by centrifuging for 10 min at 20° C. at about 5,000 xg. The cleared supernatant was made 1% w/v in sodium dodecyl sulphate (SDS) and loaded onto a preformed gradient (sucrose 15–45% w/v) in TN buffer (100 mM Tris-HCl pH 7.6, 100 mM NaCl) and spun at 100,000 xg for 2 hr at 10° C. Fractions (1 ml) were monitored at 260 nm and the fractions containing virus were extracted once with an equal volume of phenol:-chloroform (1:1) and the aqueous phase precipitated by the addition of 2 volumes ethanol, incubating overnight at −20° C. The RNA precipitate was pelleted by spinning at 5,000 xg for 30 min at 4° C. The supernatant was discarded, the pellet drained and then dissolved in 0.5 ml TNES buffer (10 mM Tris-HCl pH 7.6, 150 mM NaCl, 1 mM EDTA, and 0.2% w/v SDS). This solution was loaded onto a preformed sucrose gradient (5–25%) in TNES and centrifuged at 200,000 xg for 3.5 hr at 20° C. Fractions (0.5 ml) containing RNA sedimenting at 35S were pooled, phenol-chloroform extracted once, ethanol precipitated and redissolved as described for virus above. The resulting solution was ethanol precipitated and finally dissolved in 0.05 ml of double distilled water.

Synthesis of double stranded complementary DNA (DScDNA)

FMDV RNA (10 μg) and oligo-$dT_{(12-18)}$primer (0.5 μg; obtained from Collaborative Research) were incubated at 30° C. for 2 hr in a final volume of 100 μl containing 0.4 mM dithiothreitol, 8 mM $MgCl_2$, 50 mM Tris-HCl pH 8.1 148 mM NaCl, 0.2 mM dATP (2.5 Ci/m mole [$\alpha^{32}$P]-dATP; obtained from Radiochemical Centre, Amersham), 0.2 mM dTTP, 0.2 mM dCTP, 0.2 mM dGTP, 4 mM $Na_4P_2O_7$ and 28 units AMV reverse transcriptase (supplied by Dr. J. Beard, Life Sciences Inc., Florida). The reaction was stopped by adding EDTA (20 mM) and SDS (0.2% w/v). A sample (2%) of this terminated reaction mixture was spotted on 2.5 cm DE81 paper discs (obtained from Whatman). These were washed extensively in 5% (w/v) $Na_2HPO_4$, followed by a brief wash (5 min) in distilled water before drying and scintillation counting. From this procedure, a total yield of approximately 2 μg of cDNA was calculated. The remainder of the reaction mixture was phenol-chloroform extracted and ethanol precipitated as described above except that sodium acetate was added to 0.2 mM before addition of the ethanol. The desiccated pellet was dissolved in 100 μl 0.1M NaOH and incubated at 70° C. for 20 min to remove the template i.e. FMDV RNA. The solution was neutralised with acetic acid and the cDNA resolved from degraded RNA by passing through a column (100×15 mm) of bead-f phenol-chloroform. THe desiccated pellet was resuspended to a final volume of 90 μl in 50 mM Tris-HCl pH 8.3 20 mM dithiothreitol, 10 mM $MgCl_2$, 0.4 mM dCTP, 0.4 dGTP, 0.4 mM dATP (5.5 Ci/m mole [$\alpha^{32}$P]-dATP; Radiochemical Centre, Amersham), 0.4 mM dTTP, and 36 units AMV reverse transcriptase. After 4 hr incubation at 45° C. the reaction was stopped by the addition of EDTA (20 mM) and SDS (0.2% w/v). The mixture was phenol-chloroform extracted, NaCl was added to 0.2M and the mixture precipitated with 2 volumes of ethanol overnight at −20° C. The desiccated pellet was resuspended in 200 μl of 50 mM NaCl, 0.1% w/v SDS and passed through a Sephadex G100 column as described above. The excluded peak was ethanol precipitated in the presence of 200 μg glycogen carrier. DE81 paper disc analysis, as described above, indicated the second strand synthesis was about 60% of the maximum theoretical yield. The desiccated pellet from ethanol precipitation was resuspended in a final volume of 200 μl Si buffer (25 mM sodium acetate (pH 4.6), 150 mM NaCl, and 1 mM $ZnSO_4$). A 28 μl sample of this (sample A) was stored at −20° C. while the remainder (sample B) was incubated with 5 units $S_1$ nuclease (obtained from Sigma) for 30 min at 37° C. The reaction was stopped by extraction with phenol-chloroform and the aqueous phase precipitated with ethanol. The desiccated pellet was resuspended in 20 μl $H_2O$. To check the effectiveness of the S1 nuclease treatment in removing the loops in the double-stranded cDNA, a small amount (2%) of samples A and B was heated in S1 buffer at 100° C. for 6 min, cooled to 60° C. and 3 units of S1 added at varying times (0, 0.25, 1 and 14 hr) followed by incubation at 37° C. for 30 min. Resistance to S1 was assayed by DE81 paper disc binding as described above. The results showed that greater than 53% of sample A was resistant to S1 digestion compared with less than 2% of sample B when both were incubated with S1 immediately upon cooling to 60° C. If S1 was added 0.25 h after the samples were placed at 60° C. these figures rose to 81% and 15%, respectively. Hence the initial S1 treatment had effectively cleaved the loops present after second strand synthesis.

An estimate of the size of the molecules in sample B by agarose gel electrophoresis showed them to be distributed between full length copies (i.e., approximately 8000 bp [base pairs]) down to less than 200 bp, with a mean value of 2,000–4,000 bp.

Homopolymer tailing of plasmid and double stranded cDNA (ds cDNA)

(a) dG-tailing of the vector. Approximately 7 μg of the vector, plasmid pAT153, were digested with Pst 1 endonuclease under conditions recommended by the enzyme suppliers (Boehringer). The reaction was stopped by the addition of sodium acetate to 0.3M and ethanol precipitated. The desiccated pellet was resuspended in 100 μl of dG-tailing buffer (100 mM sodium cacodylate-HCl pH 7.1), 5 mM MgCl$_2$, 50 μg/ml bovine albumin and 1 mM dGTP (200 mCi[8$^3$-H]-dGTP/m mole). To this, 2 μl (38 units) of terminal transferase (TT) were added and the reaction incubated at 37° C. Samples were removed after 2.5, 5 and 10 min. In each case the reaction was stopped by chilling on ice and adding EDTA to 20 mM. Analysis by trichloroacetic acid precipitation of a 5 μl sample from each showed that no further incorporation of $^3$H dGMP occurred after 2.5 min and that the average length of the homopolymer tail by this time was about 25 nucleotides. The remainder of the 2.5 min sample was diluted to 100 μl with TE buffer (10 mM Tris-HCl pH 8.0, 1 mM EDTA) and extracted once with an equal volume of TE-saturated phenol. The aqueous phase was extracted four times with ether; sodium acetate was added to 0.3M and the sample ethanol precipitated. The desiccated pellet was resuspended in 40 μl H$_2$O and stored at −10° C. The concentration of DNA in this final solution was estimated to be 15 μg/ml.

(b) dC-tailing of dscDNA. Approximately 0.4 μg of dscDNA in dC-tailing buffer (100 mM sodium cacodylate HCl (pH 7.1), 1 mM CoCl$_2$, 0.1 mM DTT, 50 μg/ml bovine serum albumin 0.5 mM $^3$H dCTP (600 mCi[5-$^3$H]-CTP/m mole) was incubated with 1 μl TT (19 units). Aliquots were removed after 2 and 5 min and assayed for incorporation by TCA precipitation of a 5 μl sample of each. This indicated the average length of the homopolymer tail to be about 70 nucleotides after 2 min and 160 nucleotides after 5 min. These two aliquots were pooled, phenol extracted once, ether extracted four times, ethanol precipitated, redissolved in 50 μl H$_2$O and stored at −10° C.

Transformation with annealed plasmid and dscDNA

Approximately 0.12 μg of dG-tailed plasmid pAT153 (0.05 pmoles) and 0.1 μg dC-tailed dscDNA (0.2-0.4 pmoles) were incubated at 65° C. for 0.5 h in 100 μl TNE Buffer (10 mM Tris-Cl pH 8.0, 200 mM NaCl, 1 mM EDTA). The temperature of the incubation was steadily dropped to 20° C. over a 4 hour period and then rapidly brought to 0° C. The solution was diluted to 200 μl containing, finally, 15 mM Tris-HCl pH 7.5, 100 mM NaCl, 10 mM MgCl$_2$, 10 mM CaCl$_2$, 0.5 mM EDTA and stored at 0° C. for about 3 hours.

A transformation competent culture of *E. coli* HB101 was prepared by inoculating 1 ml of a stationary phase culture into 65 ml L-broth (1% Difco Bacto Tryptone, 0.5% Difco Bacto Yeast Extract and 0.5% NaCl, pH 7.2) and shaking at 37° C. for about 3 h after which time the A$_{650}$ was 0.4. The cells were pelleted by spinning at 3,000 xg for 5 min at 4° C. The cells were resuspended in 25 ml of 0.1M MgCl$_2$ (0° C.) and repelleted. The pellet was resuspended in 2 ml 0.1M CaCl$_2$ (0° C.) and left for 30 min at 0° C. Approximately 0.2 ml of such transformation-competent cells were gently mixed with 0.1 ml of annealed pAT153/dscDNA and left for a further 30 min at 0° C., followed by 2 min at 42° C., and a final 30 min at 0° C. To this was added 1 ml L-broth and the transformation mix then incubated at 37° C. for 25 min. Ten 0.1 ml samples of this were spread onto L-Tc plates (L-broth plus 1.5% agar and 15 μg/ml tetracycline (obtained from Sigma)) and incubated overnight at 37° C. From these ten plates 150 tetracycline resistant colonies were obtained of which about 87% were sensitive to ampicillin (100 μg/ml; Sigma) suggesting insertion of cDNA at the Pst 1 site of pAT153.

Large scale recombinant plasmid preparation

The transformants containing the plasmids were grown in bulk by inoculating 10 ml stationary culture into 500 ml L-broth and shaking at 37° C. for about 4 h until A$_{590}$ reached about 1.0. Chloramphenicol (obtained from Sigma) was then added to 0.1 mg/ml and the cultures shaken at 37° C. overnight. After this amplification step the cells were pelleted by centrifuging at 5000 xg for 5 min at 4° C. The supernatant was disinfected and discarded, and the cell pellet resuspended in 12 ml R buffer (50 mM Tris-HCl (pH 8,0), 40 mM EDTA, 25% sucrose). Lysosyme and EDTA were than added to 1.4 mg/ml and 60 mM respectively and the suspension left on ice for 5 min. To 16 ml of this were added 30 ml Triton mix (0.1% Triton X-100, 62.5 mM EDTA, 50 mM Tris-HCl pH 8.0) and the mixture left on ice about 10 min or until viscous. The mixture was then cleared by spinning at 48,000 xg for 15 min at 4° C. The resulting supernatant was carefully decanted and 0.95 g CsCl and 0.1 ml of a 10 mg/ml solution of ethidium bromide added per ml. This was spun at 12000 xg in a Beckman 50 Ti rotor at 20° C. for 40 h. The plasmid band was visualised by long wave U.V. fluorescence and removed by syringe by piercing the side of the tube. The plasmid DNA was spun to equilibrium in a second CsCl/ethidium bromide gradient. The resulting band was extracted 4 times with propan-2-ol saturated with NaCl and H$_2$O, and then ethanol precipitated, redissolved in TE and reprecipitated. The final desiccated pellet was resuspended in 200 μl TE buffer and stored at 4° C.

Physical mapping of recombinant plasmids using restriction endonucleases

The restriction endonucleases Eco RI, Pst I, Sal I, Bgl II, and Sma I were purchased from Boehringer; Bam HI, Hind III, Hinf I, Ava I, Xba and Hinc II were purchased from Bethesda Research Laboratories and Kpn I was purchased from New England Biolabs. The purified recombinant plasmid DNA was digested by these enzymes using reaction conditions specified by the suppliers. The digestion products were analysed by electrophoresis through either a 1% agarose or a 7% acrylamide gel and were visualized by ethidium bromide staining and U.V. fluorescence. Bacteriophage lambda DNA digested with Hind III (Boehringer) and plasmid pAT153 digested with Hinf I were used as size markers.

Orientation and mapping of FMDV DNA inserted into plasmids using TI ribonuclease oligonucleotides derived from FMDV RNase T1 oligonucleotides, labelled with $^{32}$P at the 5′ end for use as probes, were prepared by two-dimensional gel electrophoresis. The oligonucleotides were either labelled before electrophoresis by the procedure of Harris (T J R Harris; *Nucleic Acids Research,* 7, 1765–1785 1979) using 1–5 μg of RNA and 1 unit of RNase T1, or were isolated from a two dimensional gel and then end-labelled. In the latter procedure, an RNase T1 digest of 100 μg of RNA labelled in vivo with $^{32}$P (D J Rowlands, T J R Harris & F Brown 1978 loc cit) was separated by two dimensional gel electrophoresis and an autoradiograph of the gel used to locate the oligonucleotides. In each procedure the oligonucleotides were eluted from the gel pieces by the crush and soak method (A Maxam & W Gilbert: *Proceedings of the National Academy of Sciences,* USA, 74, 560–564 1977). The order of the oligonucleotides on the genome is described by T J R Harris, K J H Robson & F Brown (*J General Virology,* 1980, in press).

Purified recombinant DNA was digested with restriction endonucleases, the products separated on a 1% agarose gel and then transferred to a nitrocellulose filter by the method of Southern (E M Southern: *J Molecular Biology,* 98, 503–513 1975). The filter was preincubated in hybridization buffer (40% formamide, 0.4M NaCl, 10 mM PIPES-NaOH pH 6.4, 100 μg/ml *E. coli* tRNA, 0.5% SDS, 0.04% Ficoll [synthetic high molecular weight polymer of sucrose and epichlorohydrin], 0.04% polyvinylpyrrolidone 400, 0.04% bovine albumin) at 50° C. for 2 h in a sealed plastic bag before addition of labelled RNase T1 oligonucleotides (75–150,000 cpm). After 16 h, the filter was washed at 40° C. in 2×SSC (8×250 ml over 6 h), air-dried and then autoradiographed at −70° C. using Fuji XR film and intensifying screen.

Results

Figure 2:
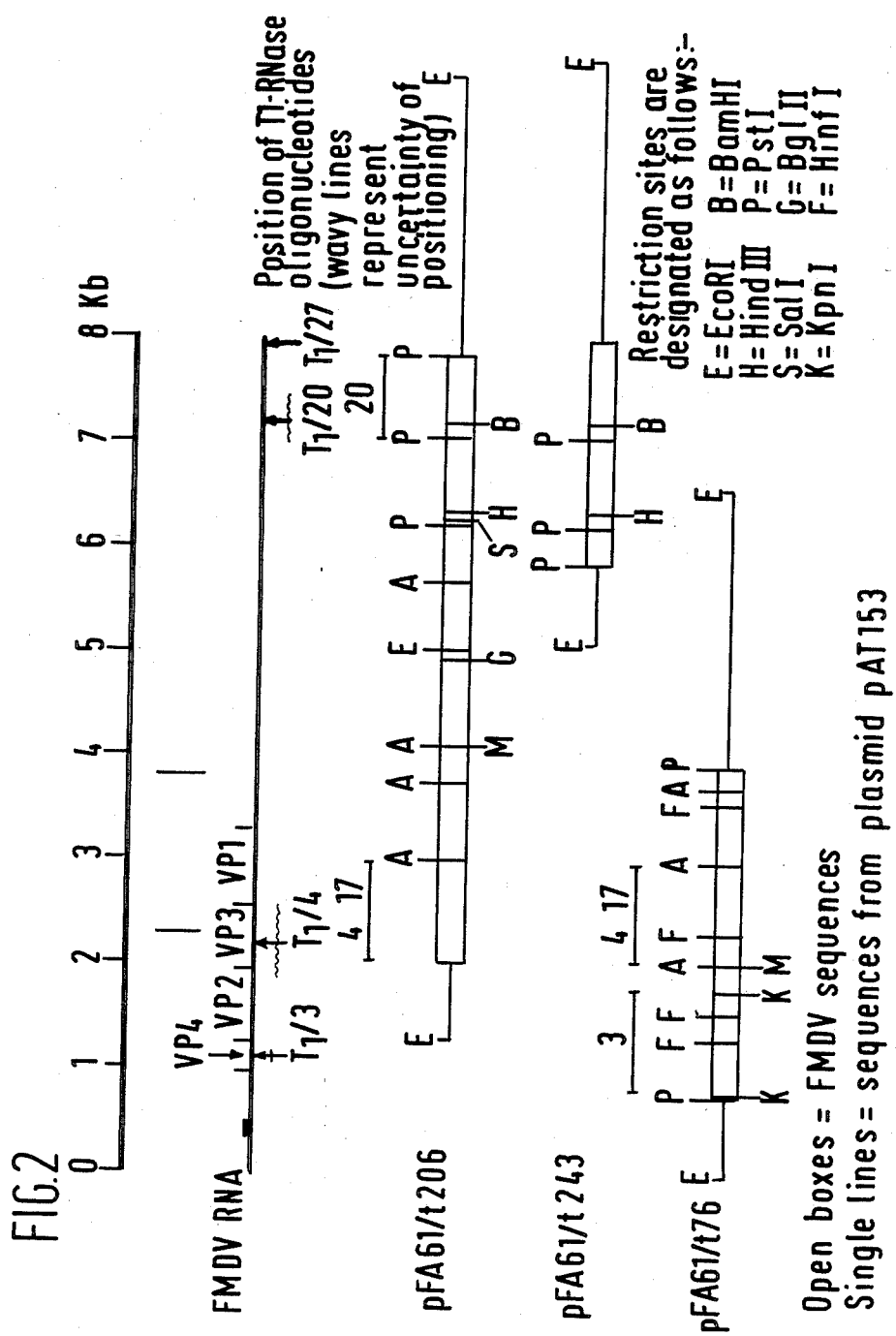
FIG. 2 is a schematic diagram of the physical maps of three recombinant plasmids compared with the genetic map of FMDV RNA.

The physical maps of three recombinant plasmids, pFA61/t206, pFA61/t243 and pFA61/76 and their alignment and correspondence with the genes of FMDV, as deduced by application of the above methods, are shown in FIG. 2.

The orientation of the largest recombinant pFA61/t206, containing a sequence of about 5,800 nucleotide pairs corresponding to about 73% of the FMDV RNA sequence, was first determined using ribonuclease T1 oligonucleotides derived from and previously mapped on the virus RNA (Harris et al, 1980 loc. cit.) T1 oligonucleotides numbers 3, 4 and 20 and 27 were particularly useful for this purpose owing to the accuracy (indicated on FIG. 2) to which their position in FMDV RNA is known. The alignment of other recombinants (for example, pFA61/76) relative to recombinant pFA61/t206 and to FMDV RNA was determined by mapping of restriction endonuclease fragments of the recombinants and hybridization with T1 oligoribonucleotides derived from the virus RNA. Two of the recombinants shown in FIG. 2 clearly contain the genetic information for several FMDV proteins including $VP_1$.

Recombinant pFA61/t206 contains $VP_1$ in an orientation for the expression of a polypeptide consisting of a fusion product of the N-terminal part of plasmid-encoded β-lactamase and a FMDV determined polypeptide.

(a) EXPRESSION

Construction of an expression vector, pXY1

Figure 14:
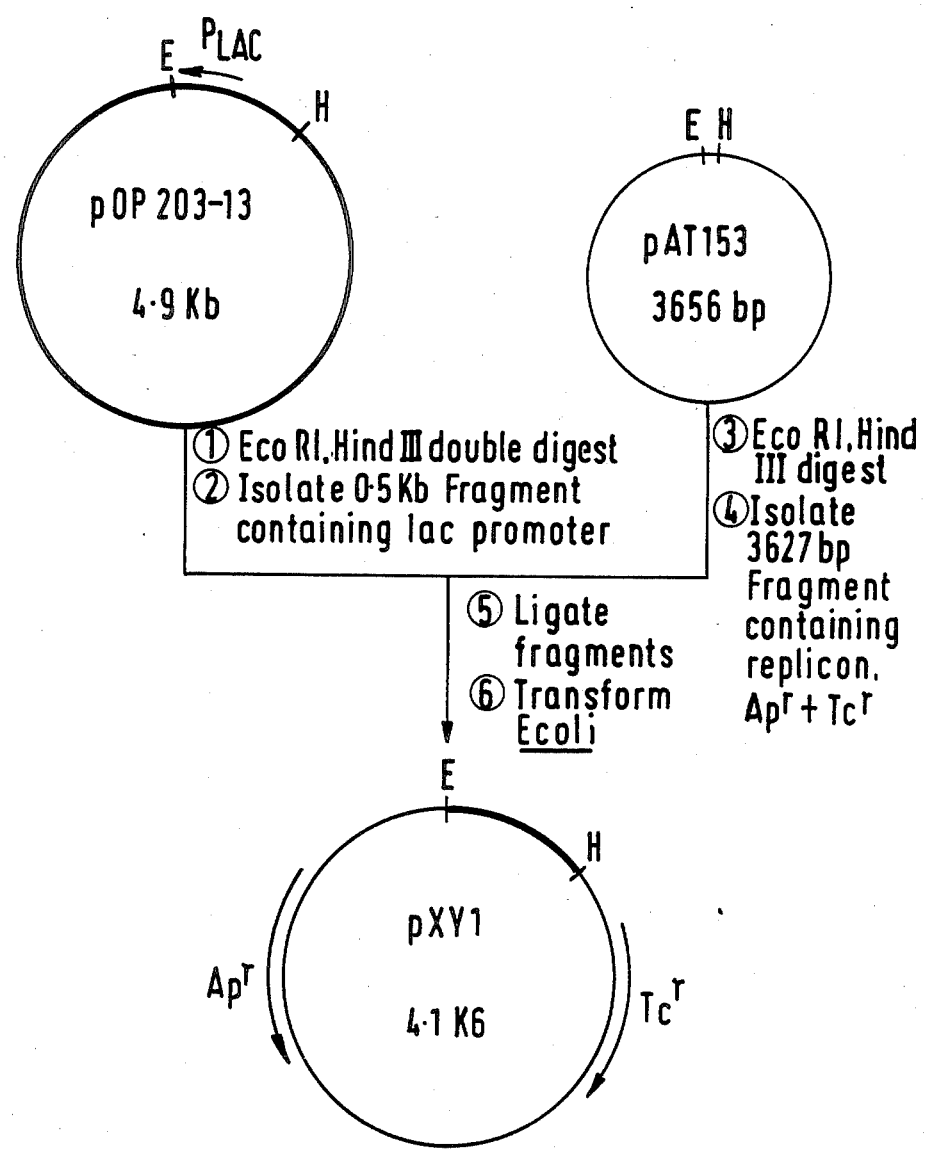
FIG. 14 is a schematic diagram of the construction of expression plasmid pXY1.

A large scale recombinant plasmid preparation of pOP 203-13 (obtainable from Forrest Fuller, Harvard University, U.S.A.) was carried out using the techniques described above. 1 μg of the purified plasmid DNA was digested with 5 units each of ECoRI and Hind III for 1 hour at 37° C. 1 μg of the plasmid pAT153 was also digested with 5 units each of EcoRI and Hind III as above. Both DNA samples were then run on an agarose gel. The 0.5 kb (kilobase pairs) DNA fragment of pOP 203-13 and the 3.6 Kb DNA fragment of pAT153 were cut out of the agarose gel and extracted by the method of Vogelstein and Gillespie, *Proc. Nat. Acad. Sci.,* 76, 615–619, 1979. The purified DNA fragments were mixed and ligated with 0.1 unit of T4 DNA ligase (Miles) for 16 hours at 15° C. The ligated DNA was used to transform a competent culture of *E. coli.* HB101 (prepared as described above) and the cells were plated out on L-Ap plates (L-broth plus 1.5% agar and 100 μg/ml ampicillin (obtained from Sigma) and incubated overnight at 37° C. Many recombinants were obtained, one of which was further characterised by restriction mapping and was designated pXY1 (FIG. 14). Fragments of FMDV ds cDNA cloned into the unique EcoR1 site of pXY1 can result in the expression of a hybrid protein consisting of the first eight amino acids of β-galactosidase, 2 amino acids from the EcoR1 site and a number of amino acids coded for by the introduced FMDV ds cDNA fragment. Hybrid proteins so produced will be under the control of the lac operon. Transcription can be induced (increased) by the addition of 30 μg/ml IPTG (isopropyl 1-thio-β-D-galactopyranoside) when the recombinant plasmid is in a host bacterium containing sufficient quantities of specific repressor protein. This can be achieved through introduction of an F′ factor containing a Lac $I^q$ mutation into the host bacterium (see Henning et al, *Proc. Nat. Acad. Sci.,* 76, 4360–4364, 1979).

(b) Introduction of FMDV ds cDNA into pXY1

2 μg of pFA61/t76 prepared as described above was digested with 6 units of EcoR1 and 1 unit of Pst I for 1 hour at 37° C. This resulted in a complete digestion with EcoR1 but only a partial digestion with Pst I. The 4.0 Kb partial digestion product containing the entire cDNA insert was isolated on an agarose gel as described previously. This was added to 2.0 μg of pXY1 (cut with 2 units each of EcoR1 and Pst I) and the DNA fragments were joined together by incubating with T4 DNA ligase (0.05 unit) for 16 hours at 15° C. The DNA was used to transform competent cultures of *E. coli* HB101 which were subsequently grown on L-Tc plates (L-broth plus 1.5% agar and 10 μg/ml tetracycline). Many recombinants were obtained that were ampicillin-sensitive, indicating the insertion of a DNA fragment into the Pst site of pXY1. One such recombinant plasmid was further characterised by restriction mapping and designated pWRL 100 (FIG. 15). This plasmid contained the lac promoter and the FMDV cDNA sequences coding for p88 in the correct orientation.

(c) Construction of expression plasmid, pWRL 1004

To achieve expression of FMDV sequences it was necessary to remove the DNA segments separating the FMDV cDNA from the lac promoter. 1 μg of purified pWRL 1000 was digested with 10 units of Sac II and ethanol precipitated. The dry DNA was redissolved in 0.1 ml of buffer (0.1M NaCl, 0.005M $MgCl_2$, 0.005M $CaCl_2$, 0.02M Tris-HCl, pH 8.1, 0.001M EDTA) and reacted with 0.2 units of nuclease Bal 31 (BRL) at 18° C. for 15 minutes. The reaction was stopped by the addition of 5 μl 0.5M EDTA. Under these conditions Bal 31 removes an average of 300 bp DNA from the ends of the linear double-stranded DNA. After ethanol precipitation the DNA was digested with 5 units of EcoR1 and again ethanol precipitated. The DNA was taken up in 40 μl Polymerase I buffer (0.06M tris-HCl, pH 7.5, 0.008M $MgCl_2$, 0.2 mM each of dATP, dTTP, dCTP, dGTP, 0.01M B-mercaptoethanol, 1 mM ATP and 1.4 units *E. coli* DNA polymerase (large fragment) and incubated 10 minutes at 10° C. The blunt ends of the linear plasmid were then ligated together with 0.4 units of T4 DNA ligase for 16 hours at 15° C. and used to transform E. coli AB2480 (obtained from P. Emmerson, University of Newcastle, U.K.) containing F' Lac I$^q$. A number of recombinants were obtained in L-Tc plates. One of the recombinants was characterised by restriction mapping and designated pWRL 1004. As a result of the restriction mapping pWRL 1004 was found to have regenerated an EcoR1 site at the junction of the lac promoter and the FMDV cDNA sequences. The plasmid-encoded proteins were examined in the UV-sensitive strain AB2480 by the "Maxicell Technique" (Sancar et al, *J. Bact.*, 137, 692–693, 1979) and pWRL 1004 was found to synthesize large proteins (50,000 daltons) coded for by the FMDV cDNA.

(d) Construction of additional expression plasmids

1 μg of pWRL was digested with 6 units of Pvu II and ligated with T4 DNA ligase in the presence of 0.2 μg of synthetic DNA fragments (containing a sequence recognized by EcoR1). The introduction of the EcoR1 "linker" (obtained from Collaborative Research) results in the introduction of a "Stop" codon four amino acids away from the C-terminus of $VP_1$. This plasmid was designated pWRL 1120 and produced a 29,000 dalton protein containing $VP_1$ when examined in "Maxicells".

2 μg of pWRL 1004 was digested with 6 units each Pvu II and Pst I and the 4.0 Kb fragment isolated from an agarose gel was described previously. Half of this DNA competent cells of *E. coli* (resulting in a plasmid pWRL 1140) while the other half was ligated in the presence of an EcoR1 linker before being used to transform *E. coli*. A plasmid of this latter type was found to have an extra EcoR1 site introduced and is designated pWRL 1130 (FIG. 16).

Results

The molecular weights and C-terminal sequences of the predominant plasmid-encoded polypeptides synthesized by pWRL 1004, 1120, 1130 and 1140 are shown in FIGS. 17 and 18. The large portion synthesized by pWRL 1004 contained sequences from the p52 polypeptide of FMDV and is unstable. The smaller proteins made in pWRL 1120 and 1130 contain primarily in $VP_1$ sequences and appeared stable in "Maxicells". The 40,000 dalton protein made by pWRL 1140 is a fusion product containing the C-terminal 104 amino acids of β-lactamase in addition to FMDV sequences and resulted in a stabilization of the polypeptide. All four of the polypeptides described above were synthesized in increased amounts when the bacteria are grown in the presence of 30 μg/ml 1PTG showing that the protein were produced under the control of the lac operon. The size of the protein produced was the same as what had been predicted.

Nucleotide sequence analysis

Figure 3:
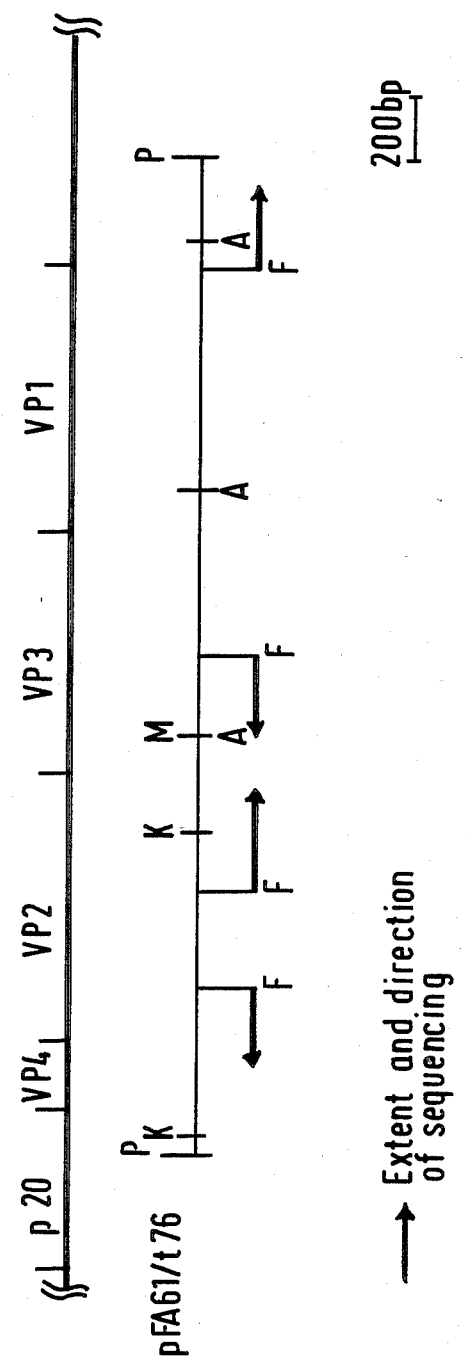
FIG. 3 is a schematic diagram of the structural gene region of FMDV RNA and shows the FMDV portion of recombinant plasmid pFA61/t76 aligned with the structural gene region of FMDV.

DNA fragments were prepared from the recombinant plasmids by digestion with appropriate restriction endonucleases. The fragments were appropriately end-labelled and the nucleotide sequences determined according to the procedures described by A Maxam and W Gilbert 1977 loc cit. From this details of the structural gene region of FMDV RNA have been determined, as shown in FIG. 3. FIGS. 4 to 10, 12 and 13 show details of the DNA and amino acid sequence in the region of the $VP_4$/$VP_2$ junction and various other parts of the structural proteins. FIG. 9 shows details of the DNA sequence of the C-terminal of $VP_3$ and N-terminal of $VP_1$. FIG. 19 shows the nucleotide sequence of the 3' end of FMDV RNA which does not code for a protein.

EXAMPLE 2

The processes used in Example 1 for preparing recombinant plasmids were repeated except that the strain of FMDV used was $O_1BFS$ (also available from Animal Virus Research Institute).

Results

Figure 11:
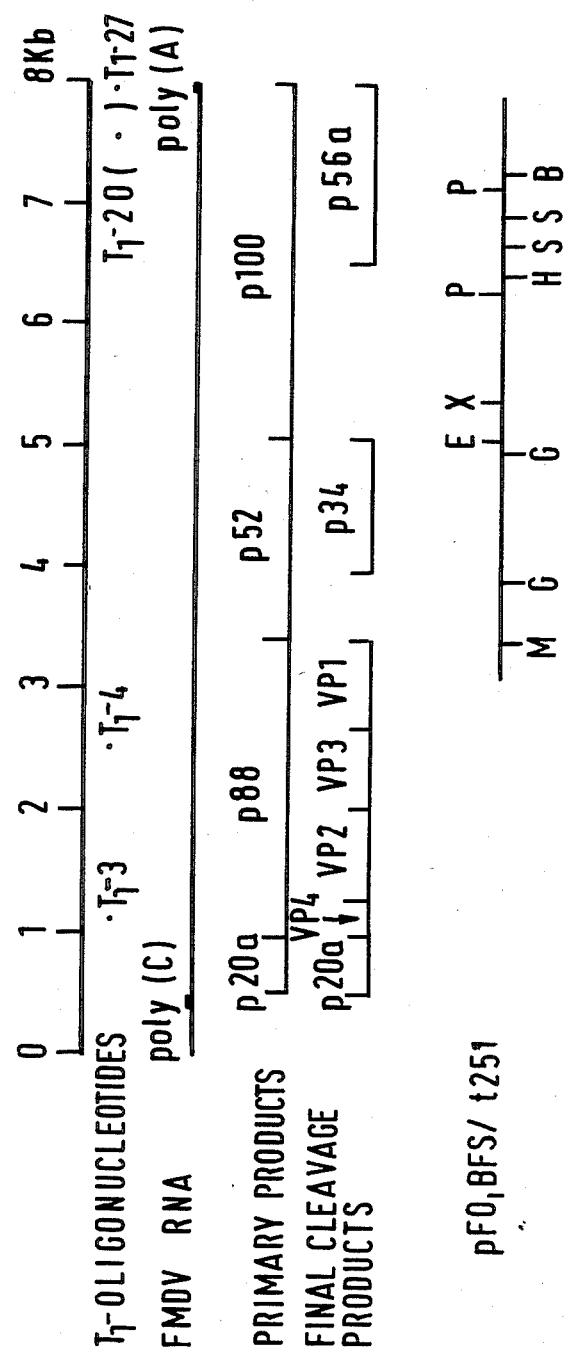
FIG. 11 is a schematic diagram of the structural gene region of FMDV RNA and shows the FMDV portion of recombinant plasmid pFO₁BFS/t251 aligned with the structural gene region of FMDV.

The physical map of a recombinant plasmid pFO$_1$BFS/t251 and its alignment and correspondence with the genes of FMDV, as deduced by application of the above methods, is shown in FIG. 11.

We claim:

1. A recombinant DNA molecule comprising an expression vector DNA sequence and a nucleotide sequence coding for a polypeptide of foot and mouth disease virus (FMDV) serotype A functionally linked to a heterologus promoter, said polypeptide consisting essentially of (i) FMDV capsid protein $VP_1$, being the capsid protein the gene for which is located closest to the 3'-end of the FMDV genome, alone or together with the whole or part of FMDV capsid protein $VP_3$, the gene for which is adjacent to that of $VP_1$, or (ii) an antigenic determinant of either of said proteins that is capable of eliciting an immune response to FMDV in a mammal.

2. A recombinant DNA molecule according to claim 1 wherein the polypeptide coded for is of FMDV serotype A, sub-type A10.

3. A host cell containing at least one recombinant cloning vehicle according to claim 1.

* * * * *